(12) United States Patent
Hamilton et al.

(10) Patent No.: US 11,504,426 B2
(45) Date of Patent: Nov. 22, 2022

(54) METHODS FOR TREATING ALLERGY AND ENHANCING ALLERGEN-SPECIFIC IMMUNOTHERAPY BY ADMINISTERING AN IL-4R ANTAGONIST

(71) Applicants: Regeneron Pharmaceuticals, Inc., Tarrytown, NY (US); Sanofi Biotechnology, Paris (FR)

(72) Inventors: Jennifer D. Hamilton, Ridgefield, CT (US); Meagan P. O'Brien, New York, NY (US); Allen Radin, New York, NY (US); Marcella Ruddy, Wellesley, MA (US); Heribert Staudinger, Green Brook, NJ (US)

(73) Assignees: REGENERON PHARMACEUTICALS, INC., Tarrytown, NY (US); SANOFI BIOTECHNOLOGY, Paris (FR)

(*) Notice: Subject to any disclaimer, the term of this patent is extended or adjusted under 35 U.S.C. 154(b) by 288 days.

(21) Appl. No.: 16/985,665

(22) Filed: Aug. 5, 2020

(65) Prior Publication Data

US 2021/0038715 A1 Feb. 11, 2021

Related U.S. Application Data

(60) Provisional application No. 62/882,992, filed on Aug. 5, 2019.

(30) Foreign Application Priority Data

Jul. 16, 2020 (EP) .................................. 20315351

(51) Int. Cl.
| | |
|---|---|
| *A61K 39/395* | (2006.01) |
| *C07K 16/28* | (2006.01) |
| *A61P 37/08* | (2006.01) |
| *A61K 36/899* | (2006.01) |

(52) U.S. Cl.
CPC ........ *A61K 39/3955* (2013.01); *A61K 36/899* (2013.01); *A61P 37/08* (2018.01); *C07K 16/2866* (2013.01)

(58) Field of Classification Search
None
See application file for complete search history.

(56) References Cited

U.S. PATENT DOCUMENTS

| | | | |
|---|---|---|---|
| 5,599,905 A | 2/1997 | Mosley | |
| 5,714,146 A | 2/1998 | Lewis | |
| 5,717,072 A | 2/1998 | Mosley | |
| 5,856,296 A | 1/1999 | Mosley | |
| 5,985,280 A | 11/1999 | Ritter | |
| 6,156,877 A | 12/2000 | Ritter | |
| 6,391,581 B1 | 5/2002 | Mosley | |
| 6,548,655 B1 | 4/2003 | Mosley | |
| 6,716,587 B2 | 4/2004 | Mosley | |
| 7,141,653 B2 | 11/2006 | Greenfeder | |
| 7,186,809 B2 | 3/2007 | Pluenneke | |
| 7,317,090 B2 | 1/2008 | Mosley | |
| 7,422,742 B2 | 9/2008 | Greenfeder | |
| 7,531,169 B2 | 5/2009 | Singh | |
| 7,605,237 B2 | 10/2009 | Stevens | |
| 7,608,693 B2 | 10/2009 | Martin | |
| 7,794,717 B2 | 9/2010 | Stevens | |
| 8,030,003 B2 | 10/2011 | Rothenberg | |
| 8,075,887 B2 | 12/2011 | Martin | |
| 8,075,897 B2 | 12/2011 | Spertini | |
| 8,092,802 B2 | 1/2012 | Stevens | |
| 8,092,804 B2 | 1/2012 | Eriksson | |
| 8,252,284 B2 | 8/2012 | Singh | |
| 8,324,192 B2 | 12/2012 | Dohil | |
| 8,337,839 B2 | 12/2012 | Martin | |
| 8,338,135 B2 | 12/2012 | Stevens | |
| 8,497,528 B2 | 7/2013 | Lee | |
| 8,604,171 B2 | 12/2013 | Singh | |
| 8,637,239 B2 | 1/2014 | Furuta | |
| 8,735,095 B2 | 5/2014 | Martin et al. | |
| 8,945,559 B2 | 2/2015 | Dix | |
| 9,238,692 B2 | 1/2016 | Dix | |
| 9,290,574 B2 | 3/2016 | Kostic | |
| 9,415,015 B2 | 8/2016 | Jacobi et al. | |
| 9,574,004 B2 | 2/2017 | Ardeleanu | |
| 10,059,771 B2 | 8/2018 | Mannent | |
| 10,066,017 B2 | 9/2018 | Mannent | |

(Continued)

FOREIGN PATENT DOCUMENTS

| | | |
|---|---|---|
| EP | 0604693 | 7/1994 |
| EP | 0367566 | 5/1997 |

(Continued)

OTHER PUBLICATIONS

ClinicalTrials.gov Identifier: NCT03558997, Jun. 15, 2018.*
DUPIXENT, Highlights of Prescribing Information, (2017).*
Yang, Eun-Seok et al., "Anti-IL-4 Receptor mAb Attenuates Allergic Airway Hyperresponsiveness (AHR) and Inflammation in Allergic Mice", J. Allergy Clin. Immunol., Poster 168, Abstracts S69, vol. 109, No. 1 (2002), 1 page.
Weber, et al. (Mar. 13, 2012) "Anti-IL-4 as a New Strategy in Allergy", Chemical immunology and Allergy, vol. 96, pp. 120-125.
Garraud, Olivier, et al., "Regulation of immunoglobulin production in hyper-IgE (Job's) syndrome", J. Allergy Clin. Immunol., Feb. 1999. (2 Pt. 1): 333-340.

(Continued)

*Primary Examiner* — Bridget E Bunner
*Assistant Examiner* — Fozia M Hamud
(74) *Attorney, Agent, or Firm* — Merchant & Gould P.C.

(57) ABSTRACT

Methods for enhancing the efficacy, safety, and/or tolerability of a grass allergen-specific subcutaneous immunotherapy (SCIT) regimen in a subject having a grass allergy are provided. Methods comprising administering to a subject in need thereof a therapeutic composition comprising an interleukin-4 receptor (IL-4R) antagonist, such as an anti-IL-4R antibody or antigen-binding fragment thereof, are provided.

28 Claims, No Drawings
Specification includes a Sequence Listing.

(56) References Cited

U.S. PATENT DOCUMENTS

| | | |
|---|---|---|
| 10,137,193 B2 | 11/2018 | Pirozzi |
| 10,370,449 B2 | 8/2019 | Graham |
| 10,392,439 B2 | 8/2019 | Stahl |
| 10,435,473 B2 | 10/2019 | Dix |
| 10,485,844 B2 | 11/2019 | Radin |
| 10,669,341 B2 | 6/2020 | Stahl |
| 10,676,530 B2 | 6/2020 | Stahl |
| 10,730,948 B2 | 8/2020 | Kostic |
| 11,034,768 B2 | 6/2021 | Amin |
| 11,053,309 B2 | 7/2021 | Radin |
| 2003/0103938 A1 | 6/2003 | Jinquan |
| 2003/0113387 A1 | 6/2003 | Tsuchida |
| 2003/0124121 A1 | 7/2003 | Pluenneke |
| 2005/0031609 A1 | 2/2005 | Hultsch |
| 2005/0074462 A1 | 4/2005 | Holmgren |
| 2005/0118176 A1 | 6/2005 | Mosley |
| 2005/0255532 A1 | 11/2005 | Ruben |
| 2005/0282181 A1 | 12/2005 | Yan |
| 2006/0013811 A1 | 1/2006 | Dina |
| 2007/0041976 A1 | 2/2007 | Pluenneke |
| 2007/0274996 A1 | 11/2007 | Carter |
| 2008/0054606 A1 | 5/2008 | Eriksson |
| 2008/0160035 A1 | 7/2008 | Stevens et al. |
| 2009/0074793 A1 | 3/2009 | Martin |
| 2009/0098142 A1 | 4/2009 | Kasaian |
| 2009/0264392 A1 | 10/2009 | Warndahl |
| 2010/0021476 A1 | 1/2010 | Stevens et al. |
| 2010/0047254 A1 | 2/2010 | Martin |
| 2010/0291107 A1 | 11/2010 | Stevens et al. |
| 2011/0195500 A1 | 8/2011 | Rothenberg |
| 2012/0004205 A1 | 1/2012 | Rothenberg |
| 2012/0052072 A1 | 3/2012 | Martin |
| 2012/0097565 A1 | 4/2012 | Dix |
| 2012/0135010 A1 | 5/2012 | Stevens et al. |
| 2012/0164080 A1 | 6/2012 | Hill |
| 2012/0207815 A1 | 8/2012 | Benhamou |
| 2013/0052190 A1 | 2/2013 | Collins |
| 2013/0078675 A1 | 3/2013 | Martin |
| 2013/0324435 A1 | 12/2013 | Rothenberg |
| 2014/0072583 A1 | 3/2014 | Ardeleanu |
| 2014/0187523 A1 | 7/2014 | Dohil |
| 2014/0271681 A1 | 9/2014 | Martin |
| 2014/0356372 A1 | 12/2014 | Stahl |
| 2015/0017176 A1 | 1/2015 | Kostic |
| 2015/0185228 A1 | 7/2015 | Reisacher |
| 2015/0246973 A1 | 9/2015 | Graham |
| 2016/0152718 A1 | 6/2016 | Kostic |
| 2016/0185866 A1 | 6/2016 | Mannent |
| 2017/0333557 A1 | 11/2017 | Ardeleanu |
| 2018/0078603 A1 | 3/2018 | Radin |
| 2018/0094069 A1 | 4/2018 | Stahl |
| 2018/0094070 A1 | 4/2018 | Stahl |
| 2018/0179288 A1 | 6/2018 | Martin et al. |
| 2019/0040126 A1 | 2/2019 | Radin |
| 2019/0169299 A1 | 6/2019 | Amin |
| 2019/0183973 A1 | 6/2019 | Hamilton |
| 2019/0345253 A1 | 11/2019 | Bansal |
| 2019/0367622 A1 | 12/2019 | Graham |
| 2020/0246416 A1 | 8/2020 | Radin |
| 2020/0299393 A1 | 9/2020 | Stahl |
| 2020/0332014 A1 | 10/2020 | Kostic |
| 2020/0345843 A1 | 11/2020 | Asrat |
| 2021/0040222 A1 | 2/2021 | Bansal |
| 2021/0163611 A1 | 6/2021 | Martin |
| 2021/0220470 A1 | 7/2021 | Bryce et al. |
| 2021/0363237 A1 | 11/2021 | Radin |
| 2021/0363264 A1 | 11/2021 | Hamilton |
| 2022/0110999 A1 | 4/2022 | Radin |

FOREIGN PATENT DOCUMENTS

| | | |
|---|---|---|
| EP | 1113818 B1 | 5/2006 |
| EP | 2022507 A1 | 2/2009 |
| EP | 1527100 | 7/2009 |
| JP | 05-246874 | 9/1993 |
| JP | 2006-131623 | 5/2006 |
| JP | 2016521713 | 7/2016 |
| RU | 2162711 | 2/2001 |
| RU | 2453303 C1 | 6/2012 |
| RU | 2552929 C1 | 6/2015 |
| WO | WO 1992/19259 | 11/1992 |
| WO | WO 1994/14975 | 7/1994 |
| WO | WO 2001/092340 | 12/2001 |
| WO | WO 2003/048083 | 6/2003 |
| WO | WO 2005/047331 | 5/2005 |
| WO | WO 2005/085284 | 9/2005 |
| WO | WO 2006/003407 | 1/2006 |
| WO | WO 2006/072564 | 7/2006 |
| WO | WO 2006/083390 | 8/2006 |
| WO | WO 2008/054606 | 5/2008 |
| WO | WO 2008/116149 | 9/2008 |
| WO | WO 2009/124954 | 10/2009 |
| WO | WO 2010/053751 | 5/2010 |
| WO | WO 2010/065557 | 6/2010 |
| WO | WO 2010/120524 | 10/2010 |
| WO | WO 2011/026966 | 3/2011 |
| WO | WO 2012/047954 | 4/2012 |
| WO | WO 2012/094643 | 7/2012 |
| WO | WO 2012/177945 | 12/2012 |
| WO | WO 2013/051928 | 4/2013 |
| WO | WO 2013/088109 | 6/2013 |
| WO | WO 2013/116287 | 8/2013 |
| WO | WO 2013/155010 | 10/2013 |
| WO | WO 2014/031610 | 2/2014 |
| WO | WO 2014/039461 | 3/2014 |
| WO | WO 2014/059178 | 4/2014 |
| WO | WO 2014/122144 | 8/2014 |
| WO | WO 2014/197470 | 12/2014 |
| WO | WO 2014/205365 | 12/2014 |
| WO | WO 2015/006571 | 1/2015 |
| WO | 2015/127229 | 8/2015 |
| WO | WO 2016/077675 | 5/2016 |
| WO | WO 2017/143270 | 8/2017 |
| WO | 2018/035393 | 2/2018 |
| WO | WO 2018/045130 | 3/2018 |
| WO | WO 2018/057776 | 3/2018 |
| WO | WO 2018/151836 | 8/2018 |
| WO | WO 2018/201051 | 11/2018 |
| WO | 2019/089473 | 5/2019 |

OTHER PUBLICATIONS

Finkelman, Fred, et al., "Regulation of murine in vivo IgG and IgE responses by a monoclonal anti-IL-4 receptor antibody", Jun. 1991;3(6); 599-607.

Chen, Ching, et al., "Enhancement and destruction of antibody function by somatic mutation: unequal occurrence is controlled by V gene combinatorial associations", The EMBO Journal vol. 15, No. 12, pp. 2784-2794, 1995.

Kussie, Paul, et al., "A Single Engineered Amino Acid Substitution Changes Antibody Fine Specificity", Journal of Immunology:152, pp. 146-152, 1994.

Takashi Yoshike, "Treatment for Atopic Dermatitis", Juntendo Medical Journal, 1999, vol. 45, No. 3, pp. 352-360, 33 pages with English translation.

Manabu Fujimoto, "Oral cyclosporin therapy for atopic dermatitis", Igaku no Ayumi, Journal of Clinical and Experimental Medicine, 2009, vol. 228, No. 1, pp. 98-102, 18 pages with English translation.

Nomura, Ichiro et al., "*Staphylococcus aureus* and Atopic Dermatitis", (2000), IRYO vol. 54, No. 2, pp. 62-66, 18 pages with English translation.

Hamilton, Jennifer et al., "Dupilumab Normalizes the Eosinophilic Esophagitis Disease Transcriptome in Adult Patients With Eosinophilic Esophagitis", May 1, 2020, Abstract, retrieved from internet on Aug. 5, 2021 at https://www.sciencedirect.com/science/article/pii/S00165085203276697via%3Dihub, 1 page.

Reed, Craig, et al., "Patient-reported outcomes in esophageal diseases", Clinical Gastroenterology and Hepatology, Elsevier, Amsterdam, NL, vol. 16. No. 3, pp. 305-310, Mar. 1, 2019.

Abonia et al. (2013) Journal of Allergy Clin Immunol "High prevalence of eosinophilic esophagitis in patients with inherited connective tissue disorders".

(56) References Cited

OTHER PUBLICATIONS

Abstracts, "Human Clinical Research and Therapeutics", Journal of Investigative Dermatology vol. 133, Supplement 1, (2013), pp. S159-S190, Abstracts 1042, and 1048 to 1050, http://apps.webofknowledge.com/full_record.do?product=WOS&search_mode=GeneralSearch&qid=2&SID=E6MDFsiCnXC9MfROx21&page=1&doc=1, 32 pages, 2013.
Aceves et al. (2009) Immunol Allergy Clin N Am 29:197-211 "Relationships Between Eosinophilic Inflammation, Tissue Remodeling, and Fibrosis in Eosinophilic Esophagitis".
Akiyama, et al., A Study on Indoor Allergens Measured in Home Environments of Adult-Asthmatic Patients, Housing Research Foundation, Research Annual Report, 1997, No. 24, Study No. 9620, 1-10.
Almagro et al., "Humanization of antibodies", (2008) Frontiers in Bioscience 13:1619-1633.
Antoniu, Sabina, "Pitrakinra, a Dual IL-4R/IL-13 Antagonist for the Potential Treatment of Asthma and Eczema", Current Opinion in Investigational Drugs 2010 11 (11): 1286-1294.
Arron et al. (2009) Am. J. Respir. Crit. Care Med. Online Abstracts Issue. 2009, B21 Airway Inflammation: New Information about Mediators and Biomarkers/Poster Discussion/Monday, May 18, 2009 "Peripheral Biomarkers of an IL-13 Induced Bronchial Epithelial Gene Signature in Asthma".
Assa'ad et al. (2011) Gastroenterology 141:1593-1604 "An Antibody Against IL-5 Reduces Numbers of Esophageal Intraepithelial Eosinophils in Children with Eosinophilic Esophagitis".
Assa'ad, Amal, What is new in the Treatment of Eosinophilic Esophagitis? Clinical and Translational Allergy 2011 (Suppl 1):S69, doi: 10.1186/2045-7022-1-S 1-S69.
Bachert et al. (2005) Drugs 65(11):1537-1552 "Pharmacological management of nasal polyposis".
Bagnasco, Diego et al., "A critical evaluation of Anti-IL-13 and Anti-IL-4 Strategies in Severe Asthma", Int. Arch Allergy Immunol 2016; 170: 122-131.
Balint and Larrick (1993) Gene 137:109-118 "Antibody engineering by parsimonious mutagenesis".
Bankhead, Charles, "IL-4 Antibody Tames Atopic Dermatitis", Medpage Today Article, https://www.medpagetoday.com/meetingcoverage/aad/37636, Mar. 3, 2013, 3 pages.
Barnes (2008) The Journal of Clinical Investigation 118(11):3546-3556 "The cytokine network in asthma and chronic obstructive pulmonary disease".
Bateman et al. (2004) Am. J. Respir. Crit. Care Med. 170:836-844 "Can guideline-defined asthma control be achieved?".
Beck et al. (Jul. 10, 2014) New England Journal of Medicine 371(2): 130-139 "Dupilumab treatment in adults with moderate-to-severe atopic dermatitis".
Beyer et al. (2002) Journal of Allergy Clin Immunol 109(4):707-713 "Human milk-specific mucosal lymphocytes of the gastrointestinal tract display a $T_H2$ cytokine profile".
Bhardwaj and Ghaffari (2012) Ann Allergy Asthma Immunol 109:155-159 "Biomarkers for eosinophilic esophagitis: a review".
Bieber, T., et al., "Atopic dermatitis: a candidate for disease-modifying strategy," Allergy 67 (2012) 969-975.
Blanchard and Rothenberg (2009) Immunol Allergy Clin N Am 29:141-148 "Chemotactic Factors Associated with Eosinophilic Gastrointestinal Diseases".
Blanchard et al. (2005) Clin Exp Allergy 35:1096-1103 "Inhibition of human interleukin-13-induced respiratory and oesophageal inflammation by anti-human-interleukin-13 antibody (CAT-354)".
Blanchard et al. (2006) The Journal of Clinical Investigation 116(2) "Eotaxin-3 and a uniquely conserved gene-expression profile in eosinophilic esophagitis".
Blanchard et al. (2007) Journal of Allergy Clin Immunol 120(6) "IL-13 involvement in eosinophilic esophagitis: Transcriptome analysis and reversibility with glucocorticoids".
Blanchard et al. (2010) The Journal of Immunology "Coordinate Interaction between IL-13 and Epithelial Differentiation Cluster Genes in Eosinophilic Esophagitis".
Blanchard et al. (2011) J Allergy Clin Immunol 127(1):208-217 "A striking local esophageal cytokine expression profile in eosinophilic esophagitis".
Blauvelt, Andrew, et al., "Long-term management of moderate-to-severe atopic dermatitis with dupilumab and concomitant topical corticosteroids (Liberty Ad Chronos): a 1-year, randomised, double-blinded, placebo-controlled, phase 3 trial," www.thelancet.com, published online May 4, 2016, http://dx.doi.org/10.1016/S0140-6736(17)31191-1.
British Society for Allergy and Clinical Immunology (BSACI) Abstracts of the 2013 Annual Meeting (dated Jul. 8-10, 2013), Clinical & Experimental Allergy, 43, 1428-1472, Nov. 22, 2013, https://onlinelibrary.wiley.com/toc/13652222/2013/43/12, 45 pages.
Brown-Whitehorn and Spergel (2010) Expert Rev Clin Immunol. 6:1:101-115 "The link between allergies and eosinophilic esophagitis: implications for management strategies".
BSACI News Report confirming BSACI conference date of Jul. 8-10, 2013, 2 pages.
Burmeister-Getz et al. (2009) J. Clin. Pharmacol. 49:1025-1036 "Human pharmacokinetics/pharmacodynamics of an interleukin-4 and interleukin-13 dual antagonist in asthma".
Burton, et al., "Direct effects of IL-4 on mast cells drive their intestinal expansion and increase susceptibility to anaphylaxis in a murine model of food allergy," Mucosal Immunology, Nov. 14, 2012, doi:10.1038/mi.2012.112.
Caldas et al. (2003) Molecular Immunology 39:941-952 "Humanization of the anti-CD18 antibody 6.7: an unexpected effect of a framework residue in binding to antigen".
Carter (2006) The Journal of Immunology 6:343-357 "Potent Antibody Therapeutics by Design".
Casset et al. (2003) Biochemical and Biophysical Research Communication 307:198-205 "A peptide mimetic of an anti-CD4 monoclonal antibody by rational design".
Chehade and Sampson (2009) Immunol Allergy Clin N Am 29:149-158 "The Role of Lymphocytes in Eosinophilic Gastrointestinal Disorders".
Cheng et al. (2012) Am J Physiol Gastrointest Liver Physiol 303:G1175-G1187 "Tissue remodeling in eosinophilic esophagitis".
Chien et al. (1989) Proc. Natl. Acad. Sci. 86:5532-5536 "Significant structural and functional change of an antigen-binding site by a distant amino acid substitution: Proposal of a structural mechanism".
Collins, Margaret H. et al., "Sa1151—Baseline Characteristics and Correlation Between Dysphagia and Disease Activity in Patients with Eosinophilic Esophagitis in a Randomized, Placebo-Controlled, Phase 2 Dupilumab Trial", abstract, Gastroenterology, vol. 154, No. 6, May 1, 2016, 1 page.
Corren et al. (2010) American Journal of Respiratory and Critical Care Medicine 181(8):788-796 "A Randomized, Controlled, Phase 2 Study of AMG 317, an IL-4R Antagonist, in Patients with Asthma".
Cortes, J.R., et al., Proton pump inhibitors inhibit IL-4 and IL-13 signaling stat6 activation, European Journal of Immunology, (Sep. 2009) vol. 39, Supp.
Davies et al. (1996) Immunotechnol. 2(3): 169-179 "Affinity improvement of single antibody VH domains: residues in all three hypervariable regions affect antigen binding".
Davis (2004) Seminars in Immunology 16:239-243 "The evolutionary and structural 'logic' of antigen receptor diversity".
De Pascalis et al. (2002) Journal of Immunology 169(6):3076-3084 "Grafting of "Abbreviated" Complementarity-Determining Regions Containing Specificity-Determining Residues Essential for Ligand Contact to Engineer a Less Immunogenic Humanized Monoclonal Antibody".
Dellon (2013) Dig Dis Sci "The Pathogenesis of Eosinophilic Esophagitis: Beyond the Eosinophil".
Dellon, Evan S. et al., "A Randomized, Double-Blind, Placebo-Controlled Trial of a Novel Recombinant, Humanized, Anti-Interleukin-13 Monoclonal Antibody (RPC4046) in Patients with Active Eosinophilic Esophagitis: Results of the HEROES Study", Oct. 14, 2016, retrieved from the Internet on Sep. 20, 2018 at: https://www.eventscribe.com/2016/ACG/QRcode.asp?Pres=178380, 3 pages.

(56) References Cited

OTHER PUBLICATIONS

Desreumaux et al. (1996) Gastroenterology 110:768-774 "Interleukin 3, Granulocyte-Macrophage Colony-Stimulating Factor, and Interleukin 5 in Eosinophilic Gastroenteritis".
Durham, Andrew L. et al., "Targeted anti-inflammatory therapeutics in asthma and chronic obstructive lung disease", Airway Disease Section, Nat'l. Heart and Lung Institute, Imperial College London, UK, published Aug. 12, 2015, 12 pages.
European Notice of Opposition in Application 13765844.9, dated Feb. 22, 2019, 34 pages.
Fillon et al. (2009) Immunol Allergy Clin N Am 29:171-178 "Epithelial Function in Eosinophilic Gastrointestinal Diseases".
Foote and Winter (1992) J. Mol. Biol. 224:487-499 "Antibody Framework Residues Affecting the Conformation of the Hypervariable Loops".
Foroughi et al. (2007) J Allergy Clin Immunol 120(3): 594-601 "Anti-IgE Treatment of Eosinophil Associated Gastrointestinal Disorders".
Franciosi and Liacouras (2009) Immunol Allergy Clin N Am 29:19-27 "Eosinophilic Esophagitis".
Garriga, A., "71st Annual Meeting of the American Academy of Dermatology (AAAD) . . . Miami Beach, FL, Mar. 1-5, 2013", Drugs of the Future 2013, 38(4): 275-279, Apr. 2013, https://journals.prous.com/journals/servlet/xmlxls/pk_journals.xml_toc_pr?p_JournalID=2&p_IssueID=1186, 5 pages.
Gavett et al. (1997) The American Physiological Society 272(16):L253-L261 "Interleukin-4 receptor blockade prevents airway responses induced by antigen challenge in mice".
Gevaert et al. (2006) Journal of Allergy and Clinical Immunology 118(5):1133-1141 "Nasal IL-5 levels determine the response to anti-IL-5 treatment in patients with nasal polyps".
Giusti et al. (1987) Proc. Natl. Acad. Sci. 84:2926-2930 "Somatic diversification of S107 from an antiphosphocholine to anti-DNA autoantibody is due to a single base change in its heavy chain variable region".
Groves et al. (2007) AERODERM in AD Poster at St. John's Institute of Dermatology "Inhibition of IL-4 and IL-13 with an IL-4 mutein (Aeroderm) protects against flares in atopic eczema".
Grunewald et al. (1998) The Journal of Immunology 160(8):4004-4009 "An Antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo".
Gussow and Seemann (1991) Methods in Enzymology 203:99-121 "Humanization of Monoclonal Antibodies".
Hamilton, Jennifer D., et al., "Drug evaluation review: Dupilumab in atopic dermatitis," Immunotherapy (Oct. 1, 2015) 7(10), 1043-1058.
Hijnen et al. (2004) J. Allergy Clin. Immunology 113(2): 334-340 "Serum thymus and activation-regulated chemokine (TARC) and cutaneous T Cell-attracting chemokine (CTACK) levels in allergic diseases: TARC and CTACK are disease-specific markers for atopic dermatitis".
Hirano, Ikuo et al., "Dupilumab Efficacy and Safety in Adult Patients With Active Eosinophilic Esophagitis: a Randomized Double-Blind Placebo-Controlled Phase 2 Trial", Oct. 13, 2017, retrieved from the internet on Sep. 20, 2018 at: http://files.shareholder.com/downloads/REGN/6138593856x0x959724/16AF93AE-DAF8-480A-8301-311C91E8FA41/Presentation.pdf, 20 pages.
Hirano, Ikuo et al., "Sa1113-Correlation Between Esophageal Distensibility and Objective Measures of Disease in Patients with Active Eosinophilic Esophagitis: A Post HOC Analysis of a Randomized, Placebo-Controlled, Phase 2 Dupilumab Trial", abstract, Gastroenterology, vol. 154, No. 6, May 1, 2018, 1 page.
Holm et al. (2007) Molecular Immunology 44:1075-1084 "Functional mapping and single chain construction of the anti-cytokeratin 8 monoclonal antibody TS1".
Holt et al. (2003) Trends in Biotechnology 21(11):484-490 "Domain antibodies: proteins for therapy".

Hong, Judith, et al., "Management of Itch in Atopic Dermatitis," Seminars in cutaneous Medicine and Surgery, vol. 30, No. 2, May 14, 2011, pp. 71-86, XP028240445.
Hopkins (2009) Clinical Otolaryngology 34(5):447-454 "Psychometric validity of the 22-item Sinonasal Outcome Test".
Hopkins et al. (2007) Otolaryngology-Head and Neck Surgery 137(4):555-561 "The Lund-Mackay staging system for chronic rhinosinusitis: How is it used and what does it predict?"
International Investigative Dermatology, Edinburgh, Conference Posters, May 8-11, 2013, 4 pages.
Ivashkiin, V. T., et al., "Eosinophillic esophagitis," a textbook for physicians, Moscow, "AISPI RAS" JSC, Feb. 14, 2013, pp. 13-21, 57-62 No English translation. (Cited in Russian Office Action for RU Appl. No. 2016104400).
Ivashkin, V. T., et al., "Eosinophilic esophagitis: literature review and description of own survey," RJGHC, 2012, vol. 22, 1, pp. 71-81.
Jahnz-Rozyk et al. (2005) Allergy 60:685-688 "Serum thymus and activation-regulated chemokine, macrophage-derived chemokine and eotaxin as marker of severity of atopic dermatitis".
Joost, T.H. Van, "Cyclosporin in atopical dermatitis: a multicentre placebo-controlled study", Journal of the American Academy of Dermatology, (1992), vol. 27, Issue 6, Part 1, pp. 922-928.
Journal of Allergy & Clinical Immunology: Abstracts at conference; https://www.jacionline.org/issue/S0091-6749(13)X0013-2, Feb. 2013, 1 page.
Junttila et al. (2008) J. Exp. Med. 205(11):2595-2608 "Tuning sensitivity to IL-4 and IL-13: differential expression of IL-4Rα, IL-13Rα1, and Yc regulates relative cytokine sensitivity".
Jyonouchi et al. (2013) Basic Mechanisms in Allergic Disease "Invariant Natural Killer T cells in children with Eosinophilic Esophagitis".
Kagami et al. (2003) Clin. Exp. Immunology 134:309-313 "Significant elevation of serum levels of eotaxin-3/CCL26, but not of eotaxin-2/CCL24, in patients with atopic dermatitis: serum eotaxin-3/CCL26 levels reflect the disease activity of atopic dermatitis".
Kakinuma et al. (2002) Clin. Exp. Immunol 127:270-273 "Serum macrophage-derived chemokine (MDC) levels are closely related with the disease activity of atopic dermatitis".
Kakinuma, Takashi et al. (2001) J. Allergy Clin. Immunol. 107(3):535-541 "Thymus and activation-regulated chemokine in atopic dermatitis: Serum thymus and activation-regulated chemokine level is closely related with disease activity".
Kakkar, Tarundeep et al. (2011) Pharmaceutical Research 28(10):2530-2542 "Population PK and IgE Pharmacodynamic Analysis of a Fully Human Monoclonal Antibody Against IL4 Receptor".
Katial (2009) Immunol Allergy Clin N Am 29:119-127 "Biomarkers for Nononcologic Gastrointestinal Disease".
Kelly and Liu (2014) World Allergy Organization Journal 7(S1):P8 "Poster 1013: IL-4R alpha antibody inhibits IgE production and airway remodeling in mouse model of house dust mite-induced eosinophilic asthma".
Kim et al. (2004) J Allergy Clin Immunol 114(6): 1449-1455 "Rebound eosinophilia after treatment of hypereosinophilic syndrome and eosinophilic gastroenteritis with monoclonal anti-IL-5 antibody SCH55700".
Konikoff et al. (2006) Gastroenterology 131:1381-1391 "A Randomized, Double-Blind, Placebo-Controlled Trial of Fluticasone Propionate for Pediatric Eosinophilic Esophagitis".
Kopf et al. (1993) Letters to Nature 362:245-248 "Disruption of the murine IL-4 gene blocks Th2 cytokine responses".
Kostic et al. (2010) Clinical Immunology 135:S105-S106 "A Fully Human IL4Rα Antibody for Inhibition of IL-4/IL-13-driven TH2 Responses in Allergic Disease".
Kottyan et al. (2014) Nature Genetics "Genome-wide association analysis of eosinophilic esophagitis provides insight into the tissue specificity of this allergic disease".
Kulis et al. (2011) J. Allergy Clin Immunol 127:81-88 "Single-tree nut immunotherapy attenuates allergic reactions in mice with hypersensitivity to multiple tree nuts".
Leung et al. (2003) The New England Journal of Medicine 348:986-993 "Effect of Anti-IgE Therapy in Patients with Peanut Allergy".
Leung et al. (2004) The Journal of Clinical Investigation 113(5): 651-657 "New insights into atopic dermatitis".

(56) References Cited

OTHER PUBLICATIONS

Lezcano-Meza et al. (2003) Allergy 58(10):1011-1017 "Interleukin (IL)-4 and to a lesser extent either IL-13 or interferon-gamma regulate the production of eotaxin-2/CCL24 in nasal polyps".
Liacouras et al. (2011) J Allergy Clin Immunol 128(1) "Eosinophilic esophagitis: Updated consensus recommendations for children and adults".
Lin et al. (2007) Clinical Reviews in Allergy & Immunology 33(3): 167-177 "Role of Bacterial Pathogens in Atopic Dermatitis".
Liu et al. (1999) Gene Therapy 6:1258-1266 "Hydrodynamics-based transfection in animals by systemic administration of plasmid DNA".
Lucendo and Sanchez-Cazalilla (2012) Expert Rev. Clin. Immunol. 8(8):733-745 "Adult versus pediatric eosinophilic esophagitis: important differences and similarities for the clinician to understand".
Ludmila and Xia (2014) World Allergy Organization Journal 7(1):P8 "Poster 1013: IL-4R alpha antibody inhibits IgE production and airway remodeling in mouse model of house dust mite-induced eosinophilic asthma".
Lwin et al. (2011) Modern Pathology 24:556-563 "Eosinophilic gastritis: histopathological characterization and quantification of the normal gastric eosinophil content".
MacCallum et al. (1996) J. Mol. Biol. 262:732-745 "Antibody-antigen Interactions: Contact Analysis and Binding Site Topography".
Maliszewski et al. (1994) Proc. Soc. Exp. Biol. Med. 206(3):233-237 "In vivo biological effects of recombinant soluble interleukin-4 receptor".
Mannon et al. (2012) GUT 61 (12):1765-1773 "Interleukin 13 and its role in gut defence and inflammation".
Mariuzza et al. (1987) Ann. Rev. Biophys. Biophys. Che. 16:139-159 "The Structural Basis of Antigen-Antibody Recognition".
Martel, Britta C., et al., "Translational animal Models of Atopic Dermatitis for Preclinical Studies," Yale Journal of Biology and Medicine 90 (2017), pp. 389-402.
Masterson et al. (2011) Curr Opin Gastroenterol. 27(6):515-522 "Update on clinical and immunological features of eosinophilic gastrointestinal diseases".
Mathias, et al., "IgE-mediated systemic anaphylaxis and impaired tolerance to food antigens in mice with enhanced IL-4 receptor signaling," Journal of Allergy and Clinical Immunology, 2011, vol. 127, No. 3, 795-805, e1-e6.
Mishra and Rothenberg (2003) Gastroenterology 125:1419-1427 "Intratracheal IL-13 Induces Eosinophilic Esophagitis by an IL-5, Eotaxin-1, and STAT6-Dependent Mechanism".
Mishra et al. (2001) J Clin. Invest. 107:83-90 "An etiological role for aeroallergens and eosinophils in experimental esophagitis".
Mishra et al. (2002) The Journal of Immunology 168:2464-2469 "IL-5 Promotes Eosinophil Trafficking to the Esophagus".
Moldoveanu et al. (2009) Journal of Inflammation Research 2:1-11 "Inflammatory mechanisms in the lung".
Molfino et al. (2012) Clinical & Experimental Allergy 42(5):712-737 "Molecular and clinical rationale for therapeutic targeting of interleukin-5 and its receptor".
Morioka et al. (2009) British Journal of Dermatology 160(6):1172-1179 "IL-4/IL-13 antagonist DNA vaccination successfully suppresses Th2 type chronic dermatitis".
Mueller, Thomas D et al., "Structure, binding, and antagonists in the IL-4/IL-13 receptor system", Biochimica et Biophysica Acta (2002) 237-250.
Müller et al. (1993) Journal of Immunology 150:5576-5584 "Th2 cells mediate IL-4-dependent local tissue inflammation".
Nadeau et al. (2011) J. Allergy Clin. Immunol 127(6) Letters to the Editor "Rapid oral desensitization in combination with omalizumab therapy in patients with cow's milk allergy".
Nadeau, et al., "Oral Immunotherapy and Anti-IgE Antibody-Adjunctive Treatment for Food Allergy," Immunology and Allergy clinics of North America, 2012, vol. 32, No. 1, 111-133.
Nguyen et al. (2011) Immunological Reviews 242(1):258-271 "Immune modulation for treatment of allergic disease".

Nguyen, Tran Hoai et al., "FutureForms of Immunotherapy and Immunomodulators in Allergic Disease", Immunol Allergy Clin N Am 31 (2011); 343-365.
Niederberger (2009) Immunology Letters 122:131-133 "Allergen-specific immunotherapy".
Niranjan et al. (2013) Immunology and Cell Biology pp. 1-8 "Pathogenesis of allergen-induced eosinophilic esophagitis is independent of interleukin (IL)-13".
Noel et al. (2004) The New England Journal of Medicine 351:940-941 "Eosinophilic Esophagitis".
Novartis (2013) QAX576 "A double blinded, randomized, placebo-controlled trial of intravenous QAX576 in the treatment of eosinophilic esophagitis".
Oetjen, Landon K., et al., "Sensory Neurons Co-opt Classical Immune Signaling Pathways to Mediate Chronic Itch," Sep. 21, 2017, Cell 171, 217-228.
Oh et al. (2010) Eur Respir Rev 19(115):46-54 "Investigational therapeutics targeting the IL-4/IL-13/STAT-6 pathway for the treatment of asthma".
Ohno et al. (1985) Proc. Natl. Acad. Sci. USA 82:2945-2949 "Antigen-binding specificities of antibodies are primarily determined by seven residues of $V_H$".
Ong (2012) Expert Opinion on Emerging Drugs 17(2):129-133 "Editorial update on emerging treatments of atopic dermatitis".
Otani et al. (2013) Journal of Allergy and Clinical Immunology 131 (6): 1576-1582 "Anti-IL-5 therapy reduces mast cell and IL-9 cell numbers in pediatric patients with eosinophilic esophagitis".
Otulana et al. (2011) Am. J. Respir. Crit. Care Med. 183:A6179 "A Phase 2b Study of Inhaled Pitrakinra, An IL-4R/IL-13 Antagonist, Successfully Identified Responder Subpopulations of Patients with Uncontrolled Asthma".
Oyoshi et al. (2009) Advances in Immunology 102:135-226 "Cellular and Molecular Mechanisms in Atopic Dermatitis".
Paton, D. M., "Dupilumab: human monoclonal antibody against IL-4Ralpha for moderate to severe atopic dermatitis," Drugs Today, vol. 53, No. 9, Sep. 1, 2017, pp. 477-487, XP055465888.
Pesek, Robert D. et al., "Emerging drugs for eosinophilic esophagitis", Expert Opinion on Emerging Drugs, vol. 23, No. 2, Apr. 3, 2018, 12 pages.
Peserico et al. (2008) British Journal of Dermatology 158:801-807 "Reduction of relapses of atopic dermatitis with methylprednisolone aceptonate cream twice weekly in addition to maintenance treatment with emollient: a multicentre, randomized, double-blind, controlled study".
Petry et al. (2012) Anais Brasileiro De Dermatologia 87(5)732-733 "Bacterial skin colonization and infections in patients with atopic dermatitis".
Prieto and Richter (2013) Curr Gastroenterol Rep 15:324 "Eosinophilic Esophagitis in Adults: an Update on Medical Management".
Prussin et al. (2009) J Allergy Clin Immunol. 124(6): 1326-1332 "Eosinophilic gastrointestinal disease and peanut allergy are alternatively associated with IL-5+ and IL-5-TH2 responses".
Rafi et al. (2010) Allergy and Asthma Proceedings 31(1):76-83 "Effects of omalizumab in patients with food allergy".
Rayapudi et al. (2010) Journal of Leukocyte Biology 88 "Indoor insect allergens are potent inducers of experimental eosinophilic esophagitis in mice".
Receptos, Inc. 2013 Annual Report.
Ring et al. (2012) J. Eur. Acad. Dermatol. Venereol. 26(8):1045-1060 "Guidelines for treatment of atopic eczema (atopic dermatitis) Part 1".
Roitt et al. (2001) Mosby—Harcourt Publishers Limited, Immunology—Sixth Edition "Antigen Presentation" pp. 110-111.
Roll et al. (2006) J. Investig Allergol Clin Immunol 16(2):79-85 "Safety of specific immunotherapy using a four-hour ultra-rush induction scheme in bee and wasp allergy".
Romaniuk, L.I., "Allergen-specific immunotherapy: mechanisms, methods and efficacy", Clinical Immunology, Allergology and Infectology, 2012, special issue, pp. 44-47. (with English translation of the cited portion).
Rothenberg (2004) J Allergy Clin Immunol 113(1):11-28 "Eosinophilic gastrointestinal disorders (EGID)".

(56) References Cited

OTHER PUBLICATIONS

Rothenberg (2009) Gastroenterology 137:1238-1249 "Biology and Treatment of Eosinophilic Esophagitis".
Rothenberg, Marc E. et al., "Intravenous anti-IL-13 mAb QAX576 for the Treatment of eosinophilic esophagitis", Journal of Allergy and Clinical Immunology, vol. 135, No. 2, Feb. 1, 2015, pp. 500-507.
Rudikoff et al. (1982) Proc. Natl. Acad. Sci. 79:1979-1983 "Single amino acid substitution altering antigen-binding specificity".
Russian Official Action from Russian Federation for RU Application 2016104400, dated Oct. 6, 2017, with translation, 4 pages.
Saeki, Hidehisa, "Guidelines for Management of Atopic Dermatitis", (Advances in Medicine, Special Issue, 2009, vol. 228(1):75-79 in part), cited in the Japanese Patent Application No. 2015-531149.
Sampson et al. (2011) J. Allergy Clin Immunol. 127(5) Letters to the Editor, "A phase II, randomized, double-blind, parallel-group, placebo-controlled oral food challenge trial of Xolair (omalizumab) in peanut allergy", p. 1309-1310.
Sanofi and Regeneron Report Positive Proof-of-Concept Data for Dupilumab, an IL-4R alpha Antibody, in Atopic Dermatitis, 71st Annual Meeting of the American Academy of Dermatology (2013) http://files.shareholder.com/downloads/REGN/2689212012x0x640531/794a7e54-6904-416b-ba38-a4ccc1726852/REGN_News_2013_3_2_General_Releases.pdf.
Sanofi with Regeneron Pharmaceuticals "An Evaluation of Dupilumab in Patients with Nasal Polyposis and Chronic Symptoms of Sinusitis" Trial in Progress, Jun. 2014. ClinicalTrials.gov Identifier: NCT01920893. Retrieved from the Internet URL: http://clinicaltrials.govishow/NCT01920893 Accessed on Sep. 29, 2014.
Sanofi, "Positive Phase 2a Results of Dupilumab in Asthma in the New England Journal of Medicine," May 21, 2013, Regeneron Pharmaceuticals, Inc.
Sanofi/Regeneron Press Release, "Sanofi and Regeneron Report Positive Results with Sarilumab in First Phase 3 Rheumatoid Arthritis Registration Trial", Paris, France and Tarrytown, NY, Nov. 22, 2013, 3 pages.
Sato et al. (1993) J. Immunol. 150(7):2717-2723 "Recombinant soluble murine IL-4 receptor can inhibit or enhance IgE responses in vivo".
Scavuzzo et al. (2005) Biomedicine & Pharmacotherapy 59(6):323-9 "Inflammatory mediators and eosinophilia in atopic and non-atopic patients with nasal polyposis".
Schmidt-Weber (2012) Chem Immunol Allergy 96:120-125 "Anti-IL-4 as a New Strategy in Allergy".
Schmitt et al. (2007) J. of Allergy and Clinical Immunology 120(6):1389-1398 "What are the best outcome measurements for atopic eczema? A systematic review".
Schneider et al. (2013) J. Allergy Clin Immunol 132(6):1368-1374 "A pilot study of omalizumab to facilitate rapid oral desensitization in high-risk peanut-allergic patients".
Sekiya et al. (2002) Allergy 57:173-177 "Increased levels of a TH2-type CC chemokine thymus and activation-regulated chemokine (TARC) in serum and induced sputum of asthmatics".
Silverberg J.I., et al., "Dupilumab treatment induces rapid clinical improvement of itch in patients with moderate-to-severe atopic dermatitis" Paper presented at: American Academy of Dermatology—76th Annual Meeting; Feb. 16-20, 2018; San Diego, CA, USA.
Silverberg J.I., et al., P481, "Dupilumab treatment rapidly improves itch in patients with moderate-to-severe atopic dermatitis" An Allergy Asthma Immunol. 2017;119 (suppl 5):S95.
Simpson, E.L., et al., "Two Phase 3 Trials of Dupilumab versus Placebo in Atopic Dermatitis," The New England Journal of Medicine, Oct. 1, 2016, DOI: 10.1056/NEJMoa1610020.
Simpson, Eric L. et al., "Dupilumab therapy provides clinically meaningful improvement in patient-reported outcomes (PROs): A phase lib, randomized, placebo-controlled, clinical trial in adult patients with moderate to severe atopic dermatitis (AD)", Journal of the American Academy of Dermatology, Mosby, Inc., US, vol. 75, No. 3, Jun. 4, 2016.
Simpson, Eric L. et al., "Patient burden of moderate to severe atopic dermatitis (AD): Insights from a phase 2b clinical trial of dupilumab in adults," Journal of the American Academy of Dermatology, Mosby, Inc., US, vol. 74, No. 3, Jan. 14, 2016.
Slager et al. (2012) Journal of Allergy, Asthma and Immunology 130(2):516-522.e4 "IL-4 Receptor Polymorphisms Predict Reduction in Asthma Exacerbations During Response to an Anti IL-4 Receptor Antagonist".
Spirin (1986) Vysshaya shkola, Moscow, pp. 17-23 "Molecular Biology Ribosome structure and protein biosynthesis", original Russian article and English language translation of same provided by foreign associate handling local prosecution of Russian application No. 2011120194.
Stein et al. (2006) J Allergy Clin Immunol 118(6):1312-1319 "Anti-IL-5 (mepolizumab) therapy for eosinophilic esophagitis".
Steinke and Borish (2001) Respiratory Research 2(2):1-5 "Th2 cytokines and asthma Interleukin-4: its role in the pathogenesis of asthma, and targeting it for asthma treatment with interleukin-4 receptor antagonists".
Stone et al. (2008) Clinical & Experimental Allergy 38(12):1858-1865 "Immunomodulatory therapy of eosinophil-associated gastrointestinal diseases".
Strauman (2009) Immunol Allergy Clin N Am 29:11-18 "Clinical Evaluation of the Adult who has Eosinophilic Esophagitis".
Straumann (2005) J Allergy Clin Immunol 115(2):418-419 "Eosinophilic esophagitis: Escalating epidemiology?"
Straumann et al. (2001) J Allergy Clin Immunol 108(6):954-961 "Idiopathic eosinophilic esophagitis is associated with a $T_H2$-type allergic inflammatory response".
Straumann et al. (2009) Gut "Anti-interleukin-5 antibody treatment (mepolizumab) in active eosinophilic oesophagitis: a randomized, placebo-controlled, double-blind trial".
Tazawa et al. (2004) Arch Dermatol Res 295:459-464 "Relative importance of IL-4 and IL-13 in lesional skin of atopic dermatitis".
Tepper et al. (1990) Cell 52:457-467 "IL-4 Induces Allergic-like Inflammatory Disease and Alters T Cell Development in Transgenic Mice".
Terui, et al., "Learning from Fungus Allergy in Atopic Dermatitis Patients," Japan J. Med. Mycol, 2000, vol. 41, No. 3, 157-160.
Thaci, Diamant et al.: "Efficacy and Safety of Dupilumab in Adults with Moderate-to-Severe Atopic Dermatitis Inadequately Controlled by Topical Treatments: A Randomised, placebo-controlled, dose-ranging phase 2b trial," The Lancet, The Lancet Publishing Group, GB, vol. 387, No. 10013, Oct. 8, 2015, pp. 40-52.
Tomkinson et al. (2001) J. Immunol. 166:5792-5800 "A Murine IL-4 Receptor Antagonist that Inhibits IL-4- and IL-13-induced Responses Prevents Antigen-Induced Airway Eosinophilia and Airway Hyper-responsiveness".
Tsianakas, Athanasios et al., "Dupilumab: A Milestone in the Treatment of Atopic Dermatitis," The Lancet, The Lancet Publishing Group, GB vol. 387, No. 10013, Oct. 8, 2015.
Ul-Haq, Zaheer et al., "Interleukin-4 receptor signaling and its binding mechanism: A therapeutic insight from inhibitors tool box", Cytokine & Growth Factor Review 32 (2016) 3-15.
Vajdos et al. (2002) Journal of Molecular Biology 320(2):415-428 "Comprehensive functional maps of the antigen-binding site of an anti-ErbB2 antibody obtained with shotgun scanning mutagenesis".
Vakharia, Paras P. et al., "Monoclonal Antibodies for Atopic Dermatitis: Progress and Potential", BioDrugs (2017) 31:409-422.
Veerappan et al. (2009) Clinical Gastroenterology and Hepatology 7:420-426 "Prevalence of Eosinophilic Esophagitis in an Adult Population Undergoing Upper Endoscopy: A Prospective Study".
Vestergaard et al. (2000) The Journal of Investigative Dermatology 115(4):640-646 "A $Th_2$ Chemokine, TARC, Produced by Keratinocytes May Recruit $CLA^+CCR4^+$ Lymphocytes into Lesional Atopic Dermatitis Skin".
Virchow et al. (1994) Lung 172:313-334 "Cellular and immunological markers of allergic and intrinsic bronchial asthma".
Walker et al. (1993) Clinical and Experimental Allergy 23:145-153 "Atopic dermatitis: correlation of peripheral blood T cell activation, eosinophilia and serum factors with clinical severity".
Wang and Liu (2008) Current Opinion in Immunology 20:697-702 "The IL-17 cytokine family and their role in allergic inflammation".

(56) References Cited

OTHER PUBLICATIONS

Wang, et al., "Peanut-induced intestinal allergy is mediated through a mast cell-IgE-FceRI-IL-13 Pathway," Journal of Allergy and Clinical Immunology, 2010, vol. 126, No. 2, 306-316, e1-e12.
Wark et al. (2006) Advanced Drug Delivery Reviews 58:657-670 "Latest technologies for the enhancement of antibody affinity".
Watson et al. (2011) Allergy, Asthma & Clinical Immunology 7:S4 "Atopic dermatitis".
Weihrauch et al. (2005) Cancer Research 65:5516-5519 "Elevated Serum Levels of CC Thymus and Activation-Related Chemokine (TARC) in Primary Hodgkin's Disease: Potential for a Prognostic Factor".
Weinbrand-Goichberg et al. (2013) Immunol Res "Eosinophilic esophagitis: an immune-mediated esophageal disease".
Wenzel et al. (2007) Lancet 370:1422-1431 "Effect of an interleukin-4 variant on late phase asthmatic response to allergen challenge in asthmatic patients: results of two phase 2a studies".
Wenzel et al. (2010) European Respiratory Society, Annual Congress 2010, "ERS—Programme" pp. 3980.
Wenzel et al. (2013) New England Journal of Medicine 368(26):2455-2466 "Dupilumab in Persistent Asthma with Elevated Eosinophil Levels".
Wershil (2009) Immunol Allergy Clin N Am 29:189-195 "Exploring the Role of Mast Cells in Eosinophilic Esophagitis".
Whalley et al. (2004) British Journal of Dermatology 150:274-283 "A new instrument for assessing quality of life in atopic dermatitis: international development of the Quality of Life Index for Atopic Dermatitis (QoLIAD)".
Wilhelm and Stockinger (2011) Frontiers in Immunology 2(68) "Innate lymphoid cells and type 2 (Th2) mediated immune responses—pathogenic or beneficial?"
Wills-Karp and Finkelman (2008) Science Signaling 1(51) "Untangling the Complex Web of IL-4 and IL-13 Mediated Signaling Pathways".
Winkler et al. (2000) J. Immunol. 165(8):4505-4514 "Changing the Antigen Binding Specificity by Single Point Mutations of an Anti-p24 (HIV-1) Antibody".
Winter and Harris (1993) Immunology Today 14(6):243-246 "Humanized Antibodies".
Wong, et al., "Guidelines for the management of atopic dermatitis (eczema) for pharmacists," CPJ/RPC, Sep./Oct. 2017, vol. 150, No. 5.
Wu et al. (1999) Journal of Molecular Biology 294:151-162 "Humanization of a murine monoclonal antibody by simultaneous optimization of framework and CDR residues".
Yamanaka et al. (2011) Curr Probl Dermatol 41:80-92 "The Role of Cytokines/Chemokines in the Pathogenesis of Atopic Dermatitis".
Yan and Shaffer (2006) World J Gastroenterol 12(15):2328-2334 "Eosinophilic esophagitis: A newly established cause of dysphagia".
Zuo et al. (2010) Journal of Immunology 185:660-669 "IL-13 Induces Esophageal Remodeling and Gene Expression by an Eosinophil-Independent, IL-13R{alpha}2-Inhibited Pathway".
Zurawski et al. (1995) J. Bioi. Chem. Am. Society of Biolochemical Biologists 270(23):13869-13878 "The primary binding subunit of the human Interleukin-4 receptor is also a component of the Interleukin-13 receptor".
Kopp, M.V. et al., "Combination of omalizumab and specific immunotherapy is superior to immunotherapy in patients with seasonal allergic rhinoconjunctivitis and co-morbid seasonal allergic asthma", Clinical and Experimental Allergy, vol. 39, No. 2, pp. 271-279, published on Jan. 22, 2009.
Huang, Evie et al: "Severe Atopic Dermatitis in Children", Current Allergy and Asthma Reports, Current Science, US, vol. 18, No. 6, May 10, 2018, pp. 1-8.
Akinlade, B. et al: "Conjunctivitis in dupilumab clinical trials", British Journal of Dermatology, (Mar. 9, 2019), pp. 1-15.
Paller et al: "Early and sustained, clinically meaningful responses with dupilumab treatment in a phase 3 trial in adolescents with moderate-to-severe atopic dermatitis", Pediatric Dermatology, vol. 36, No. Suppl. 1, (Apr. 29, 2019), p. S4.
Database Embase [Online], Elsevier Science Publishers, Amsterdam, NL; (May 1, 2019), Cork M. J: "605 Efficacy and safety of dupilumab in adolescent patients with moderate-to-severe atopic dermatitis", XP002793331, Database accession No. EMB-002001809007 abstract.
Database Embase [Online], Elsevier Science Publjshers, Amsterdam, NL; (May 1, 2019), Paller, A.S.: "621 Dupilumab in adolescents with moderate-to-severe atopic dermatitis and a history of inadequate response, or intolerance to cyclosporine: subgroup analysis from a pivotal 16-week trial", XP002793332, Database accession No. EMB-002001808313, Abstract.
Regeneron 2011 Annual Report (Apr. 2011), 12 pages.
ClinicalTrials.gov archive, History of Changes for Study: NCT01548404, "Study of Dupilumab in Adult Patients with Extrinsic Moderate-to-Severe Atopic Dermatitis", (Apr. 19, 2012), 7 pages.
ClinicalTrials.gov archive, History of Changes for Study: NCT01259323, "Sequential Ascending Dose Study to Assess the Safety and Tolerability of REGN668 (SAR231893) in Patients With Atopic Dermatitis", (May 31, 2012), 6 pages.
Clinical Trials, Study NCT00676884—"A Phase Study to Investigate the Effects of Repeated Administration of AeroDerm in Subjects with Atopic Dermatitis", Aeroderm first publication of clinical study protocol in TCS resistant moderate-to-severe AD, May 13, 2008, 6 pages.
Clinical Trials, Study NCT01548404—"Study of Dupilumab in Adult Patients with Extrinsic Moderate-to-severe Atopic Dermatitis", final publication of clinical study protocol, Aug. 27, 2015, 8 pages.
Clinical Trials, Study NCT01548404—"Study of REGN668 in Adult Patients With Extrinsic Moderate-to-Severe Atopic Dermatitis", first publication of clinical study protocol, Mar. 7, 2012, 7 pages.
Clinical Trials, Study NCT01639040—"Study to Assess the Safety of REGN668 (SAR231893) Administered Concomitantly with Topical Corticosteroids (TCS) in Patients with Moderate-to-severe Atopic Dermatitis (AD)", Concomitant treatment with TCS, Jul. 11, 2012, 6 pages.
Clinical Trials Study No. NCT01312961—"Efficacy, Safety, and Tolerability of Dupilumab in Patients with Persistent Moderate to Severe Eosinophilic Asthma", In: ClinicalTrials.gov, A service of the U.S. National Institutes of Health, First Received: Mar. 11, 2011, 10 pages, Available from: https://clinicaltrials.gov/ct2/show/NCT01312961.
Chan, L.S. et al., "Expression of Interleukin-4 in the epidermis of transgenic mice results in pruritic inflammatory skin disease: an experimental animal model to study atopic dermatitis", J. Invest. Dermatol., 2001, 117: 977-983.
Phan, N.Q. et al., "Assessment of pruritis intensity: prospective study on validity and reliability of the visual analogue scale, numeric rating scale, and verbal rating scale in 471 patients with chronic pruritis", Acta. Derm. Venereol., 2012, 92: 502-507.
Marone et al., "The Intriguing Role of Interleukin 13 in the Pathophysiology of Asthma", Frontiers in Pharmacology, 2019, pp. 1-3.
Wegmann et al., "Targeting Cytokines in Asthma therapy: could IL-37 be a Solution?", Expert Review of Respiratory Medicine, 2017, vol. 11, No. 9, pp. 675-677.
Nicodeme et al., "Esophageal Distensibility as a Measure of Disease Severity in Patients with Eosinophilic Esophagitis", Clinical Gastroenterology and Hepatology, 2013, vol. 11, No. 9, pp. 1101-1107.
De Genst, Erwin et al., "Antibody repertoire development in camelids", Developmental and Comparative Immunology, 30 (2006); 187-198.
Ward, E. Sally et al., "Blinding activities of a repertoire of single immunoglobin variable domains secreted from *Escherichia coli*", Nature, 1989, 341:544-546.
Barthelemy, Pierre et al., "Comprehensive analysis of the factors contributing to the stability and solubility of autonomous human VH domains", Journal of Biological Chemistry, 2008, 283:3639-3654.
Choi, Yoonjoo et al., "Predicting antibody complementarity determining region structures without classification", Molecular Biosystems, 2011, 7:3327-334.

(56) References Cited

OTHER PUBLICATIONS

Griffiths, Andrew et al., "Human anti-self antibodies with high specificity from phage display libraries", The EMBO Journal, 1993, 12:725-734.
Klimka et al., "Human anti-CD30 recombinant antibodies by guided phage antibody selection using cell planning", British Journal of Cancer, 2000, 83:252-260.
Beiboer, Sigrid et al., "Guided selection of a pan carcinoma specific antibody reveals similar binding characteristics yet structural divergence between the original murine antibody and its human equivalent", Journal of Molecular Biology, 2000, 296:833-849.
Darsow, Ulf et al., "Pruritus and Atopic Dermatitis", Clinic Rev Allerg Immunol (2011) 41:237-244.
Buddenkotte, J. et al., "Pathophysiology and therapy of pruritis in allergic and atopic diseases", Allergy 65 (2010), 805-821.
Highlights of Prescribing Information, DUPIXENT (dupilumab) injection, for subcutaneous use Initial U.S. Approval: 2017, U.S. Food and Drug Administration (FDA), Revised Mar. 2017.
Regeneron: "Dupixent: Highlights of Prescribing Information", (Mar. 1, 2019), pp. 1-8, XP55610296, Retrieved from the Internet: URL: https://dlegnxy4jxlq3f.cloudfront.net/Regeneron/Dupixent_FPI.pdf, 8 pgs.
Regeneron: "Highlights of Prescribing Information See 17 for Patient Counseling Information and FDA-approved patient labeling. Revised: Mar. 2017 Full Prescribing Information: Contents 1 Indications and Usage 2 Dosage and Administration 2.1 Dosage 2.2 Important Administration Instructions 2.3 Preparation for Use", (Apr. 7, 2017), XP055534130, Retrieved from the Internet: URL: https://web.archive.org/web/20170407151633if_/https://www.regeneron.com/sites/default/files/Dupixent_FPI.pdf, 4 pages.
Blankestijn, Mark et al., "Could Duratumumab be used to treat severe allergy?", Journal of Allergy and Clinical Immunology, vol. 139, No. 5, Jan. 19, 2017, p. 1677-1678.e3.
Nagaraju et al., "Bortezomib treatment diminishes hazelnut-induced intestinal anaphylaxis in mice: Immunomodulation", European Journal of Immunology, vol. 46, No. 7, May 11, 2016, pp. 1727-1736.
Winter, Oliver et al., "Pathogenic Long-Lived Plasma Cells and Their Survival Niches in Autoimmunity, Malignancy, and Allergy", The Journal of Immunology, vol. 189, No. 11, Nov. 19, 2012, pp. 5105-5111.
Cork et al., "An open-label phase IIa trial assessing the pharmacokinetics, safety and efficacy of dupilumab in a paediatric population with moderate-to-severe atopic dermatitis", P94, British Association of Dermatologists, Jul. 2017, 177 (Suppl. 1), pp. 25-77.
ClinicalTrials.gov Identifier: NTC02407756; Last Update posted Aug. 22, 2016, A Study to Determine the Safety and Tolerability of Dupilumab (REGN668/SAR231893) in Patients Aged >6 to <18 Years With Atopic Dermatitis (Eczema), 11 pages.
Dupixent (dupilumab) Injection, for Subcutaneous Use, Patient Information, Issued Mar. 2017, 34 pages.
Carr, Warner, "Topical Calcineurin Inhibitors for Atopic Dermatitis: Review and Treatment Recommendations", Pediatric Drugs, 2013, vol. 15, pp. 303-310.
Siegfried et al., "Use of dupilumab in pediatric atopic dermatitis: Access, dosing, and implications for managing severe atopic dermatitis", Pediatric Dermatology, vol. 36, No. 1, Jan. 2019, pp. 172-176.
Schmid, J.M. et al., "Basophil Sensitivity Decreases During the Updosing on SCIT in Subjects Allergic to Grass Pollen", Journal of Allergy and Clinical Immunology, vol. 127, No. S2, Feb. 1, 2011, p. AB203.
Regeneron Pharmaceuticals et al., "Dupilumab as an Adjunct for Subcutaneous Grass Immunotherapy", Jun. 26, 2019, retrieved from Internet at: https://clinicaltrials.gov/ct2/history/NCT03558997?A=4&B=4&C=merged#StudyPageTop, retrieved on Oct. 20, 2020, 10 pgs.
Regeneron Pharmaceuticals et al., "Dupilumab as an Adjunct for Subcutaneous Grass Immunotherapy", May 11, 2020, retrieved from Internet at: https://clinicaltrials.gov/ct2/history/NCT03558997?V_5=View#StudyPageTop, retrieved on Oct. 20, 2020, 46 pgs.
Corren, J. et al., "Effects of combined treatment with allergen immunotherapy and dupliumab on nasal allergen challenge and tolerability in immunotherapy", Allergy, Jun. 6, 2020, p. 78.
Linden, Carey et al., "Analysis of allergen specific IgE cut points to cat and dog in the Childhood Allergy Study", Annals of Allergy, Asthma & Immunology, 2011, 106.2: 153-158. e2.
Wenzel et al. (Jul. 2, 2016) "Dupilumab efficacy and safety in adults with uncontrolled persistent asthma despite use of medium-to-high-dose inhaled corticosteroids plus a long-acting beta2 agonist: a randomised double-blind placebo-controlled pivotal phase 2b dose-ranging trial," Lancet. 388:31-44.
Waccholz et al., "Detection of Allergen-Specific IgE Antibody Responses", 2005, Journal of Immunotoxicology, 1:3-4, 189-199.
Janeway, Jr. et al., Immunobiology, 3rd Edition, 1997, Garland Publishing Inc., pp. 11:1-11:22.
Kharkevich, D.A., Pharmacology (Farmakologiya: A Scholarly Manual), 10th Ed., Moscow: GEOTAR—Media, 2010, pp. 73-74 and pp. 846-847, with English translation of cited pages, 12 pages total.
Krasnyuk et al., "Pharmaceutical Technology: Technology of Dosage Forms: A Textbook for College and University Students", 2nd standard edition, Moscow: Akademiya Publishing Center, 2006, p. 8-9, with English translation of cited pages, 7 pages total.
Bergmann, M.M. et al., "Evaluation of Food Allergy in Patients With Atopic Dermatitis", J Allergy Clin Immunol, 1, pp. 22-28, Jan. 1, 2013.
Igelman, Sean et al., "Off-label use of dupilumab for pediatric patients with atopic dermatitis: A multicenter retrospective review", Journal of the American Academy of Dermatology, Mosby, Inc., US, vol. 82, No. 2, Oct. 10, 2019, pp. 407-411.
Ayars, Andrew G. et al., "Pharmacologic Therapies in Pulmonology and Allergy", 2016 Med Clin N Am 100(4):851-868.
Mashkovsky, M.D., Moscow, 2001 Medicines, 14th edition, v1:8-9. (Cited in RU Application 2019109062 received on Dec. 24, 2020).
Russian Office Action and Search Report in Application 2019109062, received Dec. 24, 2020, with English translation, 32 pages.
Gong, J.Q. et al., "Skin Colonization by *Staphylococcus aureus* in patients with eczema and atopic dermatitis and relevant combined topical therapy: a double-blind multicentre randomized controlled trial", British Journal of Dermatology, No. 155, pp. 680-687 (2006), Mar. 28, 2006.
Kim et al., "Engineering of anti-human interleukin-4 receptor alpha antibodies with potent antagonistic activity", Scientific Reports, 2019, vol. 9, Article No. 7772, pp. 1-12.
Radin et al., "First-in-Human Study of REGN668/SAR231893 (IL-4Rα mAb): Safety, Tolerability and Biomarker Results of a Randomized, Double-Blind, Placebo-Controlled, Single Ascending Dose Study in Healthy Volunteers", J. Allergy Clin. Immunol., 2013, vol. 131(2), Suppl., p. AB158, (made available on Jan. 26, 2013), 2 pgs.
Clinical Trials, Study NCT03682770—"Study in Pediatric Subjects With Peanut Allergy to Evaluate Efficacy and Safety of Dupilumab as Adjunct to AR10 Immunotherapy" Aug. 20, 2020, located at: URL:https://clinicaltrials.gov/ct2/history/NCT03682770?V_8=View#StudyPageTop, (retrieved on Mar. 10, 2022), 7 pages.
Corren, Jonathan et al., "Short-term subcutaneous allergy immunotherapy and dupilumab are well-tolerated in allergic rhinitis: A randomized trial", Journal of Asthma and Allergy, vol. 14, Aug. 16, 2021, pp. 1045-1063.
Bruton, Kelly et al., "Interrupting reactivation of immunologic memory diverts the allergic response and prevents anaphylaxis", Journal of Allergy and Clinical Immunology, vol. 147, No. 4, Dec. 15, 2020, pp. 1381-1392.
Wambre, ER, "Baseline characteristics of peanut-allergic individuals during the dupilumab as adjunct to AR101 clinical trial", Abstract, retrieved at: https://onlinelibrary.wiley.com/doi/10.1111/all.14506, Sep. 7, 2020, 1 page.
Chaker, Adam et al., "Short-term subcutaneous grass pollen immunotherapy under the umbrella of anti-IL-4: A randomized controlled trial", Journal of Allergy and Clinical Immunology, vol. 137, No. 2, Oct. 31, 2015, 19 pages.

(56) References Cited

OTHER PUBLICATIONS

Mulder, DJ et al., "Understanding eosinophilic esophagitis: the cellular and molecular mechanisms of an emerging disease", Mucosal Immunology, Mar. 2011, vol. 4, No. 2, pp. 139-147.

* cited by examiner

METHODS FOR TREATING ALLERGY AND ENHANCING ALLERGEN-SPECIFIC IMMUNOTHERAPY BY ADMINISTERING AN IL-4R ANTAGONIST

CROSS-REFERENCE TO RELATED APPLICATIONS

This application claims priority to U.S. Provisional Patent Application No. 62/882,992, filed Aug. 5, 2019, and to European Patent Application No. 20315351.5, filed Jul. 16, 2020, the contents of each of which are incorporated by reference.

SEQUENCE STATEMENT

The instant application contains a Sequence Listing, which has been submitted electronically in ASCII format and is hereby incorporated by reference in its entirety. Said ASCII copy, created on Jul. 30, 2020, is named 40848-0097USU1-SEQLISTING and is 11 kilobytes in size.

FIELD OF THE INVENTION

The present disclosure relates to the use of interleukin-4 receptor (IL-4R) antagonists to treat or reduce symptoms of allergy and to improve the efficacy and/or tolerability of allergen-specific immunotherapy regimens.

BACKGROUND

Allergies and allergic diseases are serious medical conditions with consequences ranging from non-life threatening responses that resolve over time to life threatening effects such as anaphylaxis. Allergic reactions can result from contact or exposure to a variety of products such as certain food items, insect venom, plants or plant-derived material (e.g., pollen), chemicals, drugs/medications, and animal dander.

Subcutaneous immunotherapy (SCIT) is a disease modifying treatment option for subjects with allergic rhinitis triggered by aeroallergens (such as pollen, animal dander, or dust). SCIT is recommended when pharmacological therapies are not sufficient to control symptoms. During SCIT, increasing doses of the inciting allergen are administered, followed by a maintenance dose for several years, with the goal of inducing immunological changes leading to symptom amelioration while on therapy, as well as sustained desensitization off SCIT (immune tolerance). Although SCIT can provide long-lasting protection from allergic disease, it also carries a risk of adverse reactions, has variable efficacy between subjects, and can take at least 3 years to induce immune tolerance (Durham S R, et al., *N Engl J Med*, 1999. 341(7): p. 468-75; Durham S R, et al., *J Allergy Clin Immunol*, 2012. 129(3): p. 717-725.e5; and Durham S R, et al., *J Allergy Clin Immunol*, 2016. 137(2): p. 339-349.e10). Typically, at the start of SCIT, patients receive injections of increasing doses of the allergen at weekly intervals over several weeks to months, under tightly monitored medical supervision. The gradual dose escalation enables tolerability to therapy and mitigates risk of severe hypersensitivity reactions related to allergen administration. However, side effects occur in 40-50% of patients ranging from mild reactions (e.g., swelling, injection site reaction, de novo allergic response, and urticaria) to life threatening reactions (e.g., asthma exacerbation and anaphylaxis) (Frew A J, *Clin Exp Allergy*. 2006a. 36(3): p. 251-3). Accordingly, an unmet need exists for more efficacious treatment of allergic disease and for improving the tolerability, safety, and/or efficacy of immunotherapeutic treatment strategies.

BRIEF SUMMARY

Provided herein are methods for enhancing the efficacy, tolerability, and/or safety of an allergen-specific immunotherapy in a patient having an allergy.

In one aspect, methods for inhibiting an allergen-specific IgE increase in a patient subjected to allergen-specific immunotherapy are provided. In some embodiments, the method comprises administering to the patient one or more doses of an interleukin-4 receptor (IL-4R) antagonist in combination with the allergen-specific immunotherapy. In some embodiments, the method comprises administering to the patient one or more doses of an interleukin-4 receptor (IL-4R) antagonist prior to or concurrent with the allergen-specific immunotherapy. In some embodiments, at least one dose of the IL-4R antagonist is administered prior to the start of the allergen-specific immunotherapy. In some embodiments, the IL-4R antagonist is an anti-IL-4R antibody, or an antigen-binding fragment thereof, that that specifically binds IL-4R.

In another aspect, methods for increasing the ratio of serum allergen-specific IgG4 to serum allergen-specific IgE in a patient subjected to allergen-specific immunotherapy are provided. In some embodiments, the method comprises administering to the patient one or more doses of an IL-4R antagonist in combination with the allergen-specific immunotherapy. In some embodiments, the method comprises administering to the patient one or more doses of an IL-4R antagonist prior to or concurrent with the allergen-specific immunotherapy. In some embodiments, at least one dose of the IL-4R antagonist is administered prior to the start of the allergen-specific immunotherapy. In some embodiments, the IL-4R antagonist is an anti-IL-4R antibody, or an antigen-binding fragment thereof, that that specifically binds IL-4R.

In another aspect, methods of facilitating administration of a maintenance dose (full up-titration) of an allergen-specific immunotherapy in a patient are provided. In some embodiments, the method comprises administering to the patient one or more doses of an IL-4R antagonist in combination with the allergen-specific immunotherapy. In some embodiments, the method comprises administering to the patient one or more doses of an IL-4R antagonist prior to or concurrent with the allergen-specific immunotherapy. In some embodiments, at least one dose of the IL-4R antagonist is administered prior to the start of the allergen-specific immunotherapy. In some embodiments, the IL-4R antagonist is an anti-IL-4R antibody, or an antigen-binding fragment thereof, that that specifically binds IL-4R.

In another aspect, methods of reducing or eliminating the use of epinephrine and/or oral steroids to treat a systemic reaction in a patient subjected to allergen-specific immunotherapy are provided. In some embodiments, the method comprises administering to the patient one or more doses of an IL-4R antagonist in combination with the allergen-specific immunotherapy. In some embodiments, the method comprises administering to the patient one or more doses of an IL-4R antagonist prior to or concurrent with the allergen-specific immunotherapy. In some embodiments, at least one dose of the IL-4R antagonist is administered prior to the start of the allergen-specific immunotherapy. In some embodiments, the IL-4R antagonist is an anti-IL-4R antibody, or an antigen-binding fragment thereof, that that specifically binds IL-4R.

In another aspect, methods for enhancing the efficacy, tolerability, and/or safety of a grass allergen-specific subcutaneous immunotherapy (SCIT) regimen in a subject having a grass allergy are provided. In some embodiments, the method comprising administering to the subject one or more doses of an interleukin-4 receptor (IL-4R) antagonist in combination with the SCIT regimen, wherein at least one dose of the IL-4R antagonist is administered prior to the start of the SCIT regimen. In some embodiments, the method comprising administering to the subject one or more doses of an IL-4R antagonist prior to or concurrent with the SCIT regimen, wherein at least one dose of the IL-4R antagonist is administered prior to the start of the SCIT regimen.

In some embodiments, the SCIT regimen comprises subcutaneous administration of a grass extract that is from a grass selected from the group consisting of Timothy, Bahia, Bermuda, Johnson, Kentucky bluegrass, Orchard, Redtop, Rye, Sweet Vernal, Meadow Fescue, and combinations thereof. In some embodiments, the grass extract is from Timothy grass.

In some embodiments, the SCIT regimen comprises a cluster SCIT regimen. In some embodiments, the cluster SCIT regimen comprises an up-titration regimen followed by a maintenance regimen, wherein the up-titration regimen comprises administering increasing doses of the grass extract over a period of 4 to 12 weeks (e.g., over a period of 4, 5, 6, 7, 8, 9, 10, 11, or 12 weeks, e.g., from 4-10 weeks, from 4-8 weeks, from 6-12 weeks, from 6-10 weeks, from 6-8 weeks, from 8-12 weeks, or from 8-10 weeks) and wherein the maintenance regimen comprises administering one or more maintenance doses of the grass extract at the highest dose administered during the up-titration regimen. In some embodiments, the up-titration regimen comprises administering increasing doses of the grass extract over a period of 8 weeks. In some embodiments, the maintenance regimen comprises administering maintenance doses every 1 to 4 weeks for at least 8 weeks (e.g., for at least 8 weeks, 10 weeks, 12 weeks, 14 weeks, 16 weeks, or longer). In some embodiments, the up-titration regimen comprises up-titrating from a dose of 1 bioequivalent allergy unit (BAU) to a dose of at least about 4,000 BAU (e.g., over a period of 4, 5, 6, 7, 8, 9, 10, 11, or weeks) and the maintenance regimen comprises administering one or more maintenance doses at least about 4,000 BAU. In some embodiments, the up-titration regimen comprises up-titrating from a dose of 1 bioequivalent allergy unit (BAU) to a dose of 4,000 BAU (e.g., over a period of 4, 5, 6, 7, 8, 9, 10, 11, or weeks) and the maintenance regimen comprises administering one or more maintenance doses at 4,000 BAU.

In some embodiments, the IL-4R antagonist is administered at a dose of about 75 mg to about 600 mg (e.g., at a dose of about 100 mg, about 150 mg, about 200 mg, about 250 mg, about 300 mg, about 350 mg, about 400 mg, about 450 mg, about 500 mg, about 550 mg, or about 600 mg). In some embodiments, the IL-4R antagonist is administered as an initial dose followed by one or more secondary doses, wherein each secondary dose is administered 1 to 4 weeks after the immediately preceding dose. In some embodiments, the initial dose of the IL-4R antagonist is administered from 1 to 7 days before the start of the SCIT regimen. In some embodiments, the initial dose comprises 600 mg and each secondary dose comprises 300 mg of the IL-4R antagonist.

In some embodiments, the IL-4R antagonist and the SCIT are not administered to the subject on the same day.

In some embodiments, the IL-4R antagonist is an anti-IL-4R antibody, or an antigen-binding fragment thereof, that specifically binds IL-4R. In some embodiments, the anti-IL-4R antibody or antigen-binding fragment thereof comprises the heavy chain complementarity determining regions (HCDRs) of a heavy chain variable region (HCVR) comprising the amino acid sequence of SEQ ID NO:1 and the light chain complementarity determining regions (LCDRs) of a light chain variable region (LCVR) comprising the amino acid sequence of SEQ ID NO:2. In some embodiments, the anti-IL-4R antibody or antigen-binding fragment thereof comprises a HCVR comprising the amino acid sequence of SEQ ID NO:1 and comprises a LCVR comprising the amino acid sequence of SEQ ID NO:2. In some embodiments, the anti-IL-4R antibody comprises a heavy chain comprising the amino acid sequence of SEQ ID NO:9 and a light chain comprising the amino acid sequence of SEQ ID NO:10. In some embodiments, the IL-4R antagonist is dupilumab or a bioequivalent thereof.

In some embodiments, enhancing the efficacy of the SCIT regimen comprises reducing allergic rhinitis symptoms in the subject. In some embodiments, a reduction in allergic rhinitis symptoms is measured by Total Nasal Symptom Score (TNSS) after a nasal allergen challenge with the grass extract and comprises an improvement in score for one or more of (i) congestion, (ii) itching, (iii) rhinorrhea, or (iv) sneezing, relative to a baseline score for the subject. In some embodiments, enhancing the efficacy of the SCIT regimen comprises reducing the area under the curve (AUC) for TNSS over the first hour after peak TNSS (0-1 hour post peak TNSS) is achieved after a nasal allergen challenge, relative to a baseline AUC for 0-1 hour post peak TNSS for the subject.

In some embodiments, enhancing the efficacy of the SCIT regimen comprises:

(a) increasing the amount of serum grass allergen-specific IgG4 (sIgG4) in the subject relative to SCIT monotherapy;

(b) decreasing the amount of serum grass allergen-specific IgE (sIgE) in the subject relative to SCIT monotherapy; and/or (c) increasing the ratio of sIgG4 to sIgE in the subject relative to SCIT monotherapy.

In some embodiments, administration of the IL-4R antagonist in combination with (e.g., prior to or concurrent with) the SCIT regimen reduces or inhibits the induction of sIgE during the SCIT up-titration regimen and/or the SCIT maintenance regimen.

In some embodiments, enhancing the efficacy of the SCIT regimen comprises reducing allergic conjunctivitis symptoms in the subject. In some embodiments, a reduction in allergic conjunctivitis symptoms is measured by Total Ocular Symptom Score (TOSS) after a nasal allergen challenge with the grass extract and comprises an improvement in score for one or more of (i) eye itching, (ii), red eye, (iii) eye tearing, and (iv) eye swelling/puffiness, relative to a baseline score for the subject.

In some embodiments, administration of the IL-4R antagonist in combination with (e.g., prior to or concurrent with) the SCIT regimen increases the tolerability of the SCIT regimen. In some embodiments, administration of the IL-4R antagonist in combination with (e.g., prior to or concurrent with) the SCIT regimen increases the maximum SCIT dose that is tolerated by the subject, relative to SCIT alone. In some embodiments, administration of the IL-4R antagonist in combination with (e.g., prior to or concurrent with) the SCIT regimen increases the number of SCIT doses or duration (e.g., number of days) of SCIT treatment that is tolerated by the subject, relative to SCIT alone.

In some embodiments, administration of the IL-4R antagonist in combination with (e.g., prior to or concurrent with) the SCIT regimen reduces the need for a rescue medication. In some embodiments, administration of the IL-4R antagonist in combination with (e.g., prior to or concurrent with) the SCIT regimen reduces the use of epinephrine or an oral steroid as a rescue medication.

In some embodiments, the IL-4R antagonist is contained in a container selected from the group consisting of a glass vial, a syringe, a pre-filled syringe, a pen delivery device, and an autoinjector. In some embodiments, the IL-4R antagonist is contained in a pre-filled syringe. In some embodiments, the pre-filled syringe is a single-dose pre-filled syringe. In some embodiments, the IL-4R antagonist is contained in an autoinjector. In some embodiments, the IL-4R antagonist is contained in a pen delivery device.

Other embodiments will be apparent from a review of the ensuing detailed description.

DETAILED DESCRIPTION

Before the present invention is described, it is to be understood that the invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "treat," "treating," or the like, mean to alleviate symptoms, eliminate the causation of symptoms either on a temporary or permanent basis, or to prevent or slow the appearance of symptoms of the named disorder or condition.

The terms "prevent," "preventing," or the like, as used with reference to an allergic reaction or allergic condition, refer to preventing development of allergy, an allergic reaction or an allergic condition. The term, as used herein, also includes reducing or abrogating allergen sensitization to prevent an allergic reaction. In some embodiments, the term refers to decreasing the level of serum allergen-specific IgE by at least 10%, at least 20%, at least 30%, at least 40%, or at least 50%, as compared to baseline, upon administration of an IL-4R antagonist as provided by the methods of the present disclosure.

As used herein, the term "subject in need thereof" refers to a human or non-human animal that (i) exhibits one or more symptoms or indicia of allergy, (ii) has been diagnosed with allergy to an allergen; and/or (iii) is at an increased risk for developing an allergy or an allergic response to an allergen. In certain embodiments, the term includes subjects that show allergen sensitization to one or more allergens (e.g., one or more grass allergens). In certain embodiments, the methods of the present disclosure may be used to treat subjects that show elevated levels of one or more serum biomarkers including, but not limited to, total IgE, allergen-specific IgE, thymus and activation-regulated chemokine (TARC), pulmonary and activation-regulated chemokine (PARC), lactate dehydrogenase (LDH), and periostin. For example, in some embodiments, the methods of the present disclosure comprise administering an IL-4R antagonist to patients with elevated levels of allergen-specific IgE. The terms "subject" and "patient" are used interchangeably herein.

As used herein, the terms "allergic response," "allergic reaction," "allergic symptom," and the like, include one or more signs or symptoms selected from the group consisting of urticaria (e.g., hives), angioedema, rhinitis, asthma, vomiting, sneezing, runny nose, sinus inflammation, watery eyes, wheezing, bronchospasm, reduced peak expiratory flow (PEF), gastrointestinal distress, flushing, swollen lips, swollen tongue, reduced blood pressure, anaphylaxis, and organ dysfunction/failure. An "allergic response," "allergic reaction," "allergic symptom," etc., also includes immunological responses and reactions such as, e.g., increased IgE production and/or increased allergen-specific immunoglobulin production.

The term "allergen," refers to a substance, chemical, particle or composition that is capable of stimulating an allergic response in a susceptible individual. Allergens may be contained within or derived from a food item such as, e.g., dairy products (e.g., cow's milk), egg, celery, sesame, wheat, soy, fish, shellfish, sugars (e.g., sugars present on meat such as alpha-galactose), peanuts, other legumes (e.g., beans, peas, soybeans, etc.), and tree nuts. Alternatively, an allergen may be contained within or derived from a non-food item such as, e.g., dust (e.g., containing dust mite), pollen, insect venom (e.g., venom of bees, wasps, mosquitos, fire ants, etc.), mold, animal fur, animal dander, wool, latex, metals (e.g., nickel), household cleaners, detergents, medication, cosmetics (e.g., perfumes, etc.), drugs (e.g., penicillin, sulfonamides, salicylate, etc.), therapeutic monoclonal antibodies (e.g., cetuximab), ragweed, grass and birch. In some embodiments, an allergen is contained within or derived from grass. In some embodiments, the allergen is contained within or derived from a grass selected from the group consisting of Timothy, Bahia, Bermuda, Johnson, Kentucky bluegrass, Orchard, Redtop, Rye, Sweet Vernal, Meadow Fescue, and combinations thereof. The terms "allergen" and "antigen" are used interchangeably through the disclosure.

Although any methods and materials similar or equivalent to those described herein can be used in the practice of the invention, the typical methods and materials are now described. All publications mentioned herein are incorporated herein by reference in their entirety.

Introduction

Provided herein are methods for enhancing the efficacy, tolerability, and/or safety of an allergen-specific immunotherapy in a patient having an allergy one or more doses of an interleukin-4 receptor (IL-4R) antagonist prior to or concurrent with the allergen-specific immunotherapy. As disclosed herein, it has been found that administration of an IL-4R antagonist, dupilumab, as an adjunct to immunotherapy improved the tolerability of immunotherapy as measured by the percentage of patients who completed the immunotherapy regimen, the maximum dose of immunotherapy that was tolerated, and number of patients who achieved full up-titration (maintenance dose) of the immunotherapy. Administration of the IL-4R antagonist also resulted in a reduction in the use of epinephrine or an oral steroid as a rescue medication to treat systemic reactions in patients subjected to allergen-specific immunotherapy.

Therapeutic Methods

In one aspect, methods for enhancing the efficacy and/or tolerability of a grass allergen-specific subcutaneous immunotherapy (SCIT) regimen are provided. In some embodiments, the methods comprise administering to a subject having a grass allergy one or more doses of an interleukin-4 receptor (IL-4R) antagonist prior to or concurrent with the SCIT regimen.

As used herein, "subcutaneous immunotherapy" or "SCIT" refers to the repeated subcutaneous administration of an allergen to a subject over time as means for treating or preventing allergies and allergic reactions, or to reduce or eliminate allergic responses. Typically, SCIT involves subcutaneously administering gradually increasing quantities of an allergen to the subject until a dose is reached that is effective in inducing immunologic tolerance to the allergen. In some embodiments, SCIT comprises an up-titration regimen, followed by a maintenance regimen. Generally, the up-titration regimen comprises administering increasing doses of the allergen over a period of time until an effective and safe dose is achieved, and the maintenance regimen comprises administering one or more doses of the allergen at the highest dose administered during the up-titration regimen.

A SCIT regimen can be a "conventional" SCIT regimen or an "accelerated" SCIT regimen. In some embodiments, the IL-4R antagonist is administered prior to or concurrent with a conventional SCIT regimen. Typically in conventional SCIT, increasing doses of the allergen are administered to the patient at weekly intervals over the course of several weeks to months (e.g., over 1, 2, 3, 4, 5, 6, 7, 8, 9, 10, 11, 12 months or longer), under tightly monitored medical supervision. In some embodiments, the IL-4R antagonist is administered prior to or concurrent with an accelerated SCIT regimen. Accelerated SCIT regimens accelerates the up-titration schedule of SCIT as compared to conventional SCIT, and includes "rush SCIT" and "cluster SCIT." Typically in rush SCIT, increasing dosages of the allergen are administered per day over several consecutive days (e.g., over 2 days, 3 days, 4 days, 5 days, 6 days, or one week) until the maximum tolerated dose is reached. In cluster SCIT, typically several (e.g., 2-3) increasing dosages of the allergen are administered in a single day, over nonconsecutive days until the maximum tolerated dose is reached, usually within 4 to 8 weeks. In some embodiments, an IL-4R antagonist is administered prior to or concurrent with a conventional SCIT regimen. In some embodiments, the IL-4R antagonist is administered prior to or concurrent with a cluster SCIT regimen. In some embodiments, the IL-4R antagonist is administered prior to or concurrent with a rush SCIT regimen.

In some embodiments, the SCIT regimen (e.g., conventional SCIT, rush SCIT, or cluster SCIT regimen) comprises subcutaneously administering a grass extract to the subject. In some embodiments, the grass extract is from a grass selected from the group consisting of Timothy, Bahia, Bermuda, Johnson, Kentucky bluegrass, Orchard, Redtop, Rye, Sweet Vernal, Meadow Fescue, and combinations thereof. In some embodiments, the grass extract comprises Timothy Grass extract. Grass extracts are known in the art and are also commercially available (e.g., from Greer Laboratories, Inc., Lenoir, N.C.).

In some embodiments, the efficacy, tolerability, and/or safety of an SCIT regimen is "enhanced" if one or more of the following outcomes or phenomena are observed or achieved in a subject: (1) the duration of the up-dosing phase is decreased without compromising efficacy or safety; (2) the duration of the maintenance phase is decreased without compromising efficacy or safety; (3) the number of doses of allergen administered during the up-dosing or maintenance phase is reduced without compromising efficacy or safety; (4) the frequency of allergen administration during the up-dosing or maintenance phase is reduced without compromising efficacy or safety; (5) the dose of allergen administered during the up-dosing or maintenance phase is increased without compromising efficacy or safety; (6) the frequency of allergic responses or adverse side-effects triggered by the SCIT regimen is reduced or eliminated; (7) the use of or need for conventional allergy medications (e.g., steroids, antihistamines, decongestants, anti-IgE agents, etc.) is reduced or eliminated during the up-dosing and/or maintenance phases; (8) the level of total IgE expression is reduced; (9) the level of allergen-specific IgG4 expression is increased; (10) the frequency of anaphylactic reactions is reduced or eliminated; or (11) the need for a rescue medication (e.g., epinephrine or an oral steroid) is reduced or eliminated. In some embodiments, the efficacy of a SCIT regimen is "enhanced" if a subject experiences fewer and/or less severe allergic reactions following SCIT therapy in combination with IL-4R blockade than with SCIT therapy alone. In some embodiments, the efficacy of a SCIT regimen is "enhanced" if the maximum SCIT dose that is tolerated by the subject is increased when an IL-4R antagonist is administered, relative to SCIT therapy alone. In some embodiments, the efficacy of a SCIT regimen is "enhanced" if there is a decreased need for rescue medication (e.g., epinephrine or oral steroids) for treating a systemic reaction when an IL-4R antagonist is administered, relative to SCIT therapy alone.

In another aspect, methods are provided for treating, preventing or reducing the severity of an allergic reaction or allergic symptoms in a subject having a grass allergy by administering an IL-4R antagonist. In some embodiments, the IL-4R antagonist is administered prior to or concurrent with a subcutaneous immunotherapy regimen (e.g., cluster SCIT).

In some embodiments, treatment with an IL-4R antagonist concurrent with an SCIT regimen reduces allergic rhinitis symptoms in the subject. In some embodiments, treatment reduces provoked allergic rhinitis symptoms after nasal allergen challenge (NAC) with an allergen (e.g., a grass extract). As used herein, "reducing allergic rhinitis symptoms" includes reducing the severity or duration of or eliminating one or more symptoms of allergic rhinitis in the subject, such as but not limited to sneezing, itching (of nose, eyes, ears, or palate), rhinorrhea, postnasal drip, congestion, anosmia, headache, earache, tearing, red eyes, eye swelling, and fatigue. In some embodiments, provoked allergic rhinitis symptoms after NAC are measured at an "early phase" (within the first 60 minutes after NAC) and/or at a "late phase" (at about 6 hours after NAC). In some embodiments, treatment with an IL-4R antagonist reduces early phase provoked allergic rhinitis symptoms after NAC. In some embodiments, treatment with an IL-4R antagonist reduces late phase provoked allergic rhinitis symptoms after NAC.

In some embodiments, a reduction in allergic rhinitis symptoms is measured by Total Nasal Symptom Score (TNSS). TNSS is a patient-reported composite symptom assessment of congestion, itching, rhinorrhea and sneezing in which patient-assessed symptom scores are assigned for each category for a given time point, using a four point scale (0-3), where 0 indicates no symptoms, a score of 1 for mild symptoms that are easily tolerated, 2 for awareness of symptoms which are bothersome but tolerable and 3 is reserved for severe symptoms that are hard to tolerate and interfere with daily activity. TNSS is calculated by adding the score for each of the symptoms to a total out of 12. In some embodiments, a TNSS score is measured after NAC with an allergen. In some embodiments, a baseline TNSS score is measured for a subject (e.g., during a screening visit prior to the start of treatment).

In some embodiments, an enhancement in the efficacy and/or safety of an SCIT regimen and/or a reduction in allergic rhinitis symptoms is measured by determining the area under the curve (AUC) for TNSS over the first hour after peak TNSS is achieved after a nasal allergen challenge ("0-1 hour post peak TNSS").

In some embodiments, treatment with an IL-4R antagonist concurrent with an SCIT regimen reduces allergic conjunctivitis symptoms in the subject (e.g., reduces provoked allergic rhinitis conjunctivitis after NAC with an allergen (e.g., a grass extract). As used herein, "reducing allergic conjunctivitis symptoms" includes reducing the severity or duration of or eliminating one or more symptoms of allergic conjunctivitis in the subject, such as but not limited to itchy, red, tearing, or puffy eyes. In some embodiments, a reduction in allergic conjunctivitis symptoms is measured by Total Ocular Symptom Score (TOSS). TOSS is a patient-reported composite symptom assessment of eye itching, eye redness, eye tearing or watering, and eye swelling or puffiness in which patient-assessed symptom scores are assigned for each category for a given time point, using a four-point scale (0-3), 3 being severe symptoms. TOSS is calculated by adding the score for each of the symptoms to a total out of 12. In some embodiments, a TOSS score is measured after NAC with an allergen. In some embodiments, a baseline TOSS score is measured for a subject (e.g., during a screening visit prior to the start of treatment).

In some embodiments, an enhancement in the efficacy and/or safety of an SCIT regimen and/or a reduction in allergic rhinitis symptoms is measured by determining the area under the curve (AUC) for TOSS over the first hour after peak Total Nasal Symptom Score (TNSS) is achieved after a nasal allergen challenge. In some embodiments, the methods of the disclosure reduce the AUC for TOSS over the first hour of the challenge by at least 10%, 20%, 30%, 40%, 50% or more, relative to a baseline AUC for TOSS after NAC for the subject.

In some embodiments, treatment with an IL-4R antagonist concurrent with an SCIT regimen improves the efficacy and/or safety of an SCIT regimen and/or reduces allergic rhinitis symptoms as measured by an improvement in one or more biomarkers, e.g., a biomarker associated with Type 2 immune activity and/or an allergen-specific biomarker. In some embodiments, the biomarker is a serum biomarker. In some embodiments, the biomarker is total IgE, allergen-specific IgG4, or thymus and activation-regulated chemokine (TARC).

In some embodiments, the biomarker is a biomarker of Type 2 immune activity, such as but not limited to serum TARC or serum total IgE. In some embodiments, the biomarker is an allergen-specific biomarker, e.g., a grass-specific biomarker, such as but not limited to grass-specific IgE (e.g., serum Timothy Grass sIgE) or grass-specific IgG4 (e.g., serum Timothy Grass sIgG4). In some embodiments, the methods of the disclosure decrease the level of a Type 2 biomarker or inhibit the induction of a Type 2 biomarker by SCIT. In some embodiments, administration of the IL-4R antagonist reduces or inhibits a rise in sIgE that is induced during SCIT (e.g., during the SCIT up-titration phase and/or the maintenance phase).

In some embodiments, the biomarker is grass-specific IgG4 (e.g., serum Timothy Grass sIgG4). Without being bound to a particular theory, it is hypothesized that the induction of allergen specific antibodies, especially of the IgG4 isotype, has a protective effect against IgE-mediated allergic symptoms, as IgG4 competes with IgE, blocking IgE-mediated effector cell activation, suppresses histamine release and inhibits antigen-presentation of IgE-allergen complex by dendritic and B-cells. In some embodiments, the methods of the disclosure increase the level of an allergen-specific biomarker (e.g., serum grass allergen-specific IgG4) relative to a baseline for the subject or relative to a control value.

In some embodiments, both total IgE and allergen-specific IgG4 biomarkers are measured and a ratio of the allergen-specific IgG4 marker to the total IgE marker (e.g., a ratio of grass allergen-specific IgE or IgG4 to total IgE) is calculated. In some embodiments, treatment with an IL-4R antagonist concurrent with an SCIT regimen increases the ratio of allergen-specific IgG4 to total IgE in a sample from the subject, e.g., as compared to a baseline value for the subject or as compared to a control value (e.g., from a subject treated with SCIT alone). In some embodiments, the methods of the disclosure increase the ratio of allergen-specific IgG4 to total IgE relative to a baseline for the subject or relative to a control value.

As will be appreciated by a person of ordinary skill in the art, an increase or decrease in a serum biomarker can be determined by comparing (i) the level of the biomarker measured in a subject at a defined time point after administration of the IL-4R antagonist to (ii) the level of the biomarker measured in the patient prior to the onset of treatment with the IL-4R antagonist (i.e., the "baseline measurement"). The defined time point at which the biomarker is measured can be, e.g., at about 4 hours, 8 hours, 12 hours, 1 day, 2 days, 3 days, 4 days, 5 days, 6 days, 7 days, 8 days, 9 days, 10 days, 15 days, 20 days, 35 days, 40 days, 50 days, 55 days, 60 days, 65 days, 70 days, 75 days, 80 days, 85 days, 100 days, 150 days, or more after the onset of treatment with the IL-4R antagonist.

Methods for detecting and/or quantifying a serum biomarker, such as allergen-specific IgE, total IgE, or TARC, are known in the art; kits for measuring such a biomarker are available from various commercial sources; and various commercial diagnostic laboratories offer services which provide measurement of such biomarkers as well.

For example, Phadiatop™ is a commercially available variant of serum specific or antigen-specific IgE assay test that was introduced for the screening of allergic sensitization (Merrett et al 1987, *Allergy* 17: 409-416). The test provides for simultaneous testing for serum specific IgE to a mixture of relevant allergens causing common inhalant allergies. The test gives a qualitative result, either positive or negative depending upon a fluorescence response obtained. When a patient sample gives a fluorescence response higher than or equal to the reference, a positive test result is indicated. A patient sample with a lower fluorescence response indicates a negative test result.

As another example, an exemplary assay system for measuring the level of the biomarker TARC is the TARC quantitative ELISA kit offered as Cat. No. DDN00 by R&D Systems, Minneapolis, Minn.

Treatment Populations

The methods disclosed herein include administering to a subject in need thereof an IL-4R antagonist or a pharmaceutical composition comprising an IL-4R antagonist. In some embodiments, a subject in need of treatment according to the methods disclosed herein is a subject who exhibits one or more symptoms or indicia of a grass allergy (e.g., an allergy to one or more of Timothy, Bahia, Bermuda, Johnson, Kentucky bluegrass, Orchard, Redtop, Rye, Sweet Vernal, or Meadow Fescue), (ii) has been diagnosed with allergy to a grass allergen; and/or (iii) is at an increased risk for developing a grass allergy or an allergic response to a grass allergen. In some embodiments, the subject is an adult.

In some embodiments, the subject to be treated meets one or more of the following criteria: (a) a grass allergy confirmed by a positive skin prick test (SPT) with a grass (e.g., Timothy Grass) extract (e.g., mean wheal diameter at least mm greater than a negative control); (b) a grass allergy confirmed by a positive serum grass allergen (e.g., Timothy Grass)-specific IgE (e.g., ≥0.35 KU/L); and (c) a positive NAC with a grass (e.g., Timothy Grass) extract with a peak TNSS score out of 12.

Interleukin-4 Receptor Antagonists

In some embodiments, the methods of the present disclosure comprise administering to a subject in need thereof (e.g., a subject having a grass allergy) an interleukin-4 receptor (IL-4R) antagonist or a pharmaceutical composition comprising an IL-4R antagonist. As used herein, an "IL-4R antagonist" (also referred to herein as an "IL-4R inhibitor", an "IL-4R blocker," or an "IL-4Rα antagonist") is any agent that binds to or interacts with IL-4Rα or an IL-4R ligand, and inhibits or attenuates the normal biological signaling function of a type 1 and/or a type 2 IL-4 receptor. Human IL-4Rα has the amino acid sequence of SEQ ID NO:11. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R antagonists that can be used in the methods of the present disclosure may function by blocking IL-4-mediated signaling, IL-13-mediated signaling, or both IL-4- and IL-13-mediated signaling. The IL-4R antagonists of the present disclosure may thus prevent the interaction of IL-4 and/or IL-13 with a type 1 or type 2 receptor.

Non-limiting examples of categories of IL-4R antagonists include small molecule IL-4R inhibitors, anti-IL-4R aptamers, peptide-based IL-4R inhibitors (e.g., "peptibody" molecules), "receptor-bodies" (e.g., engineered molecules comprising the ligand-binding domain of an IL-4R component), and antibodies or antigen-binding fragments of antibodies that specifically bind human IL-4Rα. As used herein, IL-4R antagonists also include antigen-binding proteins that specifically bind IL-4 and/or IL-13.

Anti-IL-4Rα Antibodies and Antigen-Binding Fragments Thereof

In certain exemplary embodiments of the present disclosure, the IL-4R antagonist is an anti-IL-4Rα antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In some embodiments, the FRs of the anti-IL-4R antibody (or antigen-binding portion thereof) are identical to the human germline sequences. In some embodiments, one or more FRs of the anti-IL-4R antibody (or antigen-binding portion thereof) are naturally or artificially modified.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed by the term "antigen-binding fragment," as used herein.

An antigen-binding fragment of an antibody will typically comprise at least one variable domain. The variable domain may be of any size or amino acid composition and will generally comprise at least one CDR that is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; $V_H$-$C_H2$-$C_H3$; (vii) $V_H$-CL; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The constant region of an antibody is important in the ability of an antibody to fix complement and mediate cell-dependent cytotoxicity. Thus, in some embodiments the isotype of an antibody may be selected on the basis of whether it is desirable for the antibody to mediate cytotoxicity.

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present disclosure using routine techniques available in the art. For example, in some embodiments the methods of the present disclosure comprise the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

In some embodiments, the antibodies used in the methods of the present disclosure are human antibodies. The term "human antibody," as used herein, is intended to include antibodies having variable and constant regions derived from human germline immunoglobulin sequences. The human antibodies of the disclosure may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present disclosure may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see, e.g., Taylor et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

An "isolated antibody" refers to an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody." An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

According to certain embodiments, the antibodies used in the methods of the present disclosure specifically bind IL-4Rα. The term "specifically binds," as used herein, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. In some embodiments, an antibody that "specifically binds" IL-4Rα binds to IL-4Rα or a portion thereof with an equilibrium dissociation constant ($K_D$) of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 1 nM, less than about 0.5 nM, less than about 0.25 nM, less than about 0.1 nM or less than about 0.05 nM, as measured in a surface plasmon resonance assay (e.g., BIAcore™ Biacore Life Sciences division of GE Healthcare, Piscataway, N.J.). In some embodiments, an antibody that specifically binds to a target antigen (e.g., IL-4Rα) can also specifically bind to another antigen, e.g., an ortholog of the target antigen. For example, in some embodiments, an isolated antibody that specifically binds human IL-4Rα exhibits cross-reactivity to other antigens, such as IL-4Rα molecules from other (non-human) species.

In some embodiments, the IL-4R antagonist is an anti-IL-4Rα antibody, or antigen-binding fragment thereof, comprising a heavy chain variable region (HCVR), light chain variable region (LCVR), and/or complementarity determining regions (CDRs) comprising any of the amino acid sequences of the anti-IL-4R antibodies as set forth in U.S. Pat. No. 7,608,693. In some embodiments, the IL-4R antagonist is an anti-IL-4Rα antibody or antigen-binding fragment thereof that comprises the heavy chain complementarity determining regions (HCDRs) of a heavy chain variable region (HCVR) comprising the amino acid sequence of SEQ ID NO:1 and the light chain complementarity determining regions (LCDRs) of a light chain variable region (LCVR) comprising the amino acid sequence of SEQ ID NO:2. In some embodiments, the IL-4R antagonist is an anti-IL-4Rα antibody or antigen-binding fragment thereof that comprises three HCDRs (HCDR1, HCDR2 and HCDR3) and three LCDRs (LCDR1, LCDR2 and LCDR3), wherein the HCDR1 comprises the amino acid sequence of SEQ ID NO:3; the HCDR2 comprises the amino acid sequence of SEQ ID NO:4; the HCDR3 comprises the amino acid sequence of SEQ ID NO:5; the LCDR1 comprises the amino acid sequence of SEQ ID NO:6; the LCDR2 comprises the amino acid sequence of SEQ ID NO:7; and the LCDR3 comprises the amino acid sequence of SEQ ID NO:8.

In some embodiments, the anti-IL-4R antibody or antigen-binding fragment thereof comprises the HCDR1, HCDR2, HCDR3, LCDR1, LCDR2, and LCDR3 of SEQ ID NOs:3, 4, 5, 6, 7, and 8, respectively, and further comprises an HCVR having at least 85% sequence identity (e.g., at least 90%, 91%, 92%, 93%, 94%, 95%, 96%, 97%, 98%, or 99% sequence identity) to the amino acid sequence of SEQ ID NO:1 and an LCVR having at least 85% sequence identity (e.g., at least 90%, 91%, 92%, 93%, 94%, 95%, 96%, 97%, 98%, or 99% sequence identity) to the amino acid sequence of SEQ ID NO:2. In some embodiments, the anti-IL-4R antibody or antigen-binding fragment thereof comprises an HCVR comprising SEQ ID NO:1 and an LCVR comprising SEQ ID NO:2.

In some embodiments, the anti-IL-4R antibody comprises a heavy chain comprising the amino acid sequence of SEQ ID NO:9. In some embodiments, the anti-IL-4R antibody comprises a light chain comprising the amino acid sequence of SEQ ID NO:10.

An exemplary antibody comprising a heavy chain comprising the amino acid sequence of SEQ ID NO:9 and a light chain comprising the amino acid sequence of SEQ ID NO:10 is the fully human anti-IL-4R antibody known as dupilumab. According to certain exemplary embodiments, the methods of the present disclosure comprise the use of dupilumab, or a bioequivalent thereof. The term "bioequivalent," as used herein with reference to dupilumab, refers to anti-IL-4R antibodies or IL-4R-binding proteins or fragments thereof that are pharmaceutical equivalents or pharmaceutical alternatives whose rate and/or extent of absorption do not show a significant difference with that of dupilumab when administered at the same molar dose under similar experimental conditions, either single dose or multiple dose. In some embodiments, the term refers to antigen-binding proteins that bind to IL-4R which do not have clinically meaningful differences with dupilumab in their safety, purity and/or potency.

Other anti-IL-4Rα antibodies that can be used in the context of the methods of the present disclosure include, e.g., the antibody referred to and known in the art as AMG317 (Corren et al., 2010, Am J Respir Crit Care Med., 181(8):788-796), or MEDI 9314, or any of the anti-IL-4Rα antibodies as set forth in U.S. Pat. Nos. 7,186,809, 7,605,237, 7,638,606, 8,092,804, 8,679,487, or 8,877,189.

In some embodiments, an anti-IL-4Rα antibody used in the methods of the present disclosure can have pH-dependent binding characteristics. For example, an anti-IL-4Rα antibody for use as disclosed herein may exhibit reduced binding to IL-4Rα at acidic pH as compared to neutral pH. Alternatively, an anti-IL-4Rα antibody for use as disclosed herein may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the $K_D$ value of the antibody binding to IL-4Rα at acidic pH to the $K_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present disclosure if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present disclosure can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Preparation of Human Antibodies

Methods for generating human antibodies in transgenic mice are known in the art. Any such known methods can be used in the context of the present disclosure to make human antibodies that specifically bind to human IL-4R.

Using VELOCIMMUNE™ technology (see, for example, U.S. Pat. No. 6,596,541, Regeneron Pharmaceuticals) or any other known method for generating monoclonal antibodies, high affinity chimeric antibodies to IL-4R are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc., using standard procedures known to those skilled in the art. The mouse constant regions are replaced with a desired human constant region to generate the fully human antibody of the disclosure, for example wild-type or modified IgG1 or IgG4. While the constant region selected may vary according to specific use, high affinity antigen-binding and target specificity characteristics reside in the variable region.

In general, the antibodies that can be used in the methods of the present disclosure possess high affinities, as described above, when measured by binding to antigen either immobilized on solid phase or in solution phase. The mouse constant regions are replaced with desired human constant regions to generate the fully human antibodies of the disclosure. While the constant region selected may vary according to specific use, high affinity antigen-binding and target specificity characteristics reside in the variable region.

In one embodiment, a human antibody or antigen-binding fragment thereof that specifically binds IL-4R and that can be used in the methods disclosed herein comprises the three heavy chain CDRs (HCDR1, HCDR2 and HCDR3) contained within a heavy chain variable region (HCVR) having an amino acid sequence of SEQ ID NO: 1, and the three light chain CDRs (LCVR1, LCVR2, LCVR3) contained within a light chain variable region (LCVR) having an amino acid sequence of SEQ ID NO: 2. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Pharmaceutical Compositions

In one aspect, the present disclosure provides methods that comprise administering an IL-4R antagonist to a subject, wherein the IL-4R antagonist (e.g., an anti-IL-4R antibody) is contained within a pharmaceutical composition that comprises one or more pharmaceutically acceptable vehicle, carriers, and/or excipients. Various pharmaceutically acceptable carriers and excipients are well-known in the art. See, e.g., Remington's Pharmaceutical Sciences, Mack Publishing Company, Easton, Pa. In some embodiments, the carrier is suitable for intravenous, intramuscular, oral, intraperitoneal, intrathecal, transdermal, topical, or subcutaneous administration.

Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. In some embodiments, a pharmaceutical composition as disclosed herein is administered intravenously. In some embodiments, a pharmaceutical composition as disclosed herein is administered subcutaneously.

In some embodiments, the pharmaceutical composition comprises an injectable preparation, such as a dosage form for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

The dose of antibody administered to a subject according to the methods of the present disclosure may vary depending upon the age and the size of the subject, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, subject progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351). Specific exemplary doses of anti-IL4R antibodies, and administration regimens involving the same, that can be used in the context of the present disclosure are disclosed elsewhere herein.

In some embodiments, a pharmaceutical composition of the present disclosure is contained within a container. Thus, in another aspect, containers comprising a pharmaceutical composition as disclosed herein are provided. For example, in some embodiments, a pharmaceutical composition is contained within a container selected from the group consisting of a glass vial, a syringe, a pen delivery device, and an autoinjector.

In some embodiments, a pharmaceutical composition of the present disclosure is delivered, e.g., subcutaneously or intravenously, with a standard needle and syringe. In some embodiments, the syringe is a pre-filled syringe. In some embodiments, a pen delivery device or autoinjector is used to deliver a pharmaceutical composition of the present disclosure (e.g., for subcutaneous delivery). A pen delivery device can be reusable or disposable. Typically, a reusable pen delivery device utilizes a replaceable cartridge that contains a pharmaceutical composition. Once the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Examples of suitable pen and autoinjector delivery devices include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™ OPTIPEN STARLET™, and OPTICLIK™ (sanofi-aventis, Frankfurt, Germany). Examples of disposable pen delivery devices having applications in subcutaneous delivery of a pharmaceutical composition of the present disclosure include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.).

In some embodiments, the pharmaceutical composition is delivered using a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533. Other delivery systems are known and can be used to administer the pharmaceutical composition, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432).

In some embodiments, the pharmaceutical composition is supplied in a container as disclosed herein (e.g., a glass vial, syringe, pen delivery device, or autoinjector) at a volume of about 0.5 mL to about 2.5 mL, e.g., about 0.7 mL, 0.8 mL, 0.9 mL, 1.0 mL, 1.1 mL, 1.15 mL, 1.2 mL, 1.25 mL, 1.3 mL, 1.4 mL, 1.5 mL, 1.6 mL, 1.7 mL, 1.75 mL, 1.8 mL, 1.9 mL, 2.0 mL, 2.1 mL, 2.2 mL, 2.25 mL, 2.3 mL, 2.4 mL, or 2.5 mL. In some embodiments, the pharmaceutical composition is contained in a volume of about 0.7 mL. In some embodiments, the pharmaceutical composition is contained in a volume of about 1.15 mL. In some embodiments, the pharmaceutical composition is contained in a volume of about 2.25 mL.

In some embodiments, pharmaceutical compositions for use as described herein are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the context of the present disclosure are disclosed, e.g., in U.S. Pat. No. 8,945,559.

Dosage

Generally, an IL-4R antagonist (e.g., anti-IL-4R antibody) is administered to a subject according to the methods of the present disclosure in a therapeutically effective amount. As used herein with reference to an IL-4R antagonist, the phrase "therapeutically effective amount" means an amount of IL-4R antagonist that results in one or more of: (a) treatment of or reduction in the severity or duration of an allergic reaction; (b) the alleviation of one or more symptoms or indicia of an allergic reaction; (c) increase in the ratio of serum allergen-specific IgG4 to serum allergen-specific IgE; (d) reduction in the level of one or more markers of Type 2 immune activity (e.g., serum TARC or total IgE); (e) reduction in the frequency of allergic responses to allergen-specific immunotherapy; and (f) reduction in provoked allergic rhinitis symptoms after nasal allergen challenge.

In the case of an anti-IL-4R antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody. In some embodiments, a therapeutically effective amount is from about 75 mg to about 600 mg. In certain embodiments, 75 mg, 100 mg, 150 mg, 200 mg, or 300 mg of an anti-IL-4R antibody is administered to a subject.

The amount of IL-4R antagonist (e.g., anti-IL-4R antibody) contained within the individual doses may be expressed in terms of milligrams of antibody per kilogram of subject body weight (i.e., mg/kg). For example, the IL-4R antagonist may be administered to a subject at a dose of about 0.0001 to about 10 mg/kg of subject body weight, e.g., at a dose of about 1 mg/kg to about 10 mg/kg, or about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg.

In some embodiments, the IL-4R antagonist (e.g., anti-IL-4R antibody) is administered to the subject in an amount that results in a serum concentration level of the antagonist of at least about 70 mg/L (e.g., at least about 75 mg/L, at least about 80 mg/L, at least about 85 mg/L, or greater) when measured after four weeks of treatment.

For SCIT, the dosage of the allergen (e.g., grass extract) that is administered increases during the up-titration regimen. In some embodiments, SCIT is administered at a starting dosage of 1 bioequivalent allergy unit (BAU) and is increased during the up-titration regimen to a target dose of about 1,000-4,000 BAU (for pasture grasses, e.g., Timothy, Johnson, Kentucky bluegrass, Orchard, Redtop, Rye, Sweet Vernal, or Meadow Fescue grasses) or to a target dose of about 300-1500 BAU (for Bermuda grass). In some embodiments, SCIT is administered at an increasing dosage that starts at 1 BAU and increases to about 1,000, about 1,500, about 2,000, about 2,500, about 3,000, about 3,500, or about 4,000 BAU. In some embodiments, following the up-titration regimen, SCIT is administered at a maintenance dose that is equal to the target dose (e.g., a target dose of about 1,000-4,000 BAU for pasture grasses or a target dose of about 300-1500 BAU for Bermuda grass). An exemplary dosage regimen for SCIT is shown in Table 1 below.

Administration Regimens

In some embodiments, the methods disclosed herein comprise administering an IL-4R antagonist to a subject at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In some embodiments, an anti-IL-4R antibody is administered once a week or one every two weeks at an amount of about 75 mg, 150 mg, 200 mg, or 300 mg.

In some embodiments, multiple doses of an IL-4R antagonist are administered to a subject over a defined time course. In some embodiments, the methods of the present disclosure comprise sequentially administering to a subject multiple doses of an IL-4R antagonist. As used herein, "sequentially administering" means that each dose of IL-4R antagonist is administered to the subject at a different point in time, e.g., on different days separated by a predetermined interval (e.g., hours, days, weeks or months). In some embodiments, the methods of the disclosure comprise sequentially administering to the patient a single initial dose of an IL-4R antagonist, followed by one or more secondary doses of the IL-4R antagonist, and optionally followed by one or more tertiary doses of the IL-4R antagonist.

The terms "initial dose," "secondary doses," and "tertiary doses," refer to the temporal sequence of administration of the IL-4R antagonist. Thus, the "initial dose" is the dose that is administered at the beginning of the treatment regimen (also referred to as the "loading dose"); the "secondary doses" are the doses that are administered after the initial dose; and the "tertiary doses" are the doses that are administered after the secondary doses. The initial, secondary, and tertiary doses may all contain the same amount of IL-4R antagonist, but generally may differ from one another in terms of frequency of administration. In certain embodiments, however, the amount of IL-4R antagonist contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an IL-4R antagonist may be administered to a subject at an initial or loading dose of about 400 mg or about 600 mg followed by one or more secondary or maintenance doses of about 75 mg to about 300 mg. In one embodiment, the initial dose and the one or more secondary doses each include 50 mg to 600 mg of the IL-4R antagonist, e.g., 100 mg, 150 mg, 200 mg, 250 mg, 300 mg, 400 mg, 500 mg, or 600 mg of the IL-4R antagonist. In some embodiments, the initial dose and the one or more secondary doses each contain the same amount of the IL-4R antagonist. In other embodiments, the initial dose comprises a first amount of the IL-4R antagonist, and the one or more secondary doses each comprise a second amount of the IL-4R antagonist. For example, the first amount of the IL-4R antagonist can be 1.5×, 2×, 2.5×, 3×, 3.5×, 4× or 5× or more than the second amount of the IL-4R antagonist. In one exemplary embodiment, an IL-4R antagonist is administered to a subject at a loading dose of about 600 mg followed by one or more maintenance doses of about 300 mg. In another exemplary embodiment, an IL-4R antagonist may be administered to a subject at a loading dose of about 400 mg followed by one or more maintenance doses of about 200 mg. In some embodiments, no loading dose is administered.

In some embodiments, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of IL-4R antagonist that is administered to a patient prior to the administration of the very next dose in the sequence with no intervening doses.

The methods of the disclosure may comprise administering to a patient any number of secondary and/or tertiary doses of an IL-4R antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In some embodiments involving multiple secondary doses, each secondary dose is administered at the same frequency as the other secondary doses. For example, each secondary dose may be administered to the patient 1 to 2 weeks after the immediately preceding dose. Similarly, in some embodiments involving multiple tertiary doses, each tertiary dose is administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In some embodiments, SCIT is administered to the subject as a cluster SCIT regimen comprising an up-titration regimen of about 4-12 weeks (e.g., from 4-10 weeks, from 4-8 weeks, from 6-12 weeks, from 6-10 weeks, from 6-8 weeks, from 8-12 weeks, or from 8-10 weeks) followed by a maintenance regimen of 4, 6, 8, 10, 12 weeks or more. In some embodiments, SCIT is administered at an increasing dosage in an up-titration regimen of about 4, 5, 6, 7, 8, 9, 10, 11, or 12 weeks followed by administration of a maintenance dosage for at least 8 weeks. In some embodiments, SCIT is administered at an increasing dosage in an up-titration regimen of 8 weeks followed by administration of a maintenance dosage for 8 weeks or longer.

In some embodiments, at least one dose of the IL-4R antagonist is administered one or more days before the start of the SCIT regimen. In some embodiments, at least one dose of the IL-4R antagonist is administered at least 1, 2, 3, 4, 5, 6, 7, 8, 9, 10 or more days before the start of the SCIT regimen. In some embodiments, a first dose of the IL-4R antagonist is administered from 1-7 days before the start of the SCIT regimen. In some embodiments, a first dose of the IL-4R antagonist is administered up to one week before the start of the SCIT regimen.

In some embodiments, the first dose of the IL-4R antagonist is administered prior to the start of the SCIT regimen and subsequent doses of the IL-4R antagonist are administered after the start of the SCIT regimen. For example, in some embodiments, an initial (loading) dose of an IL-4R antagonist is administered from 1-14, 1-10, or 1-7 days before the start of the SCIT regimen and the first secondary (maintenance) dose of the IL-4R antagonist is not administered until at least one day after the start of the SCIT regimen.

In some embodiments, more than one dose of the IL-4R antagonist is administered prior to the start of the SCIT regimen. For example, in some embodiments, an initial (loading) dose of an IL-4R antagonist and at least one secondary (maintenance) dose of the IL-4R antagonist are administered prior to the start of the SCIT regimen.

In some embodiments, the IL-4R antagonist and the SCIT are not administered to the subject on the same day.

Combination Therapies

In some embodiments, the methods of the present disclosure comprise administering to the subject the IL-4R antagonist, or the IL-4R antagonist and the SCIT regimen, in combination with one or more additional therapeutic agents. As used herein, the expression "in combination with" means that the one or more additional therapeutic agents are administered before, concurrent with, or after the IL-4R antagonist or the IL-4R antagonist and the SCIT regimen.

For example, when administered "before" the pharmaceutical composition comprising the IL-4R antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the IL-4R antagonist. When administered "after" the pharmaceutical composition comprising the IL-4R antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the IL-4R antagonist. Administration "concurrent" or with the pharmaceutical composition comprising the IL-4R antagonist means that the additional therapeutic agent is administered to the subject in a separate dosage form within less than 5 minutes (before, after, or at the same time) of administration of the pharmaceutical composition comprising the IL-4R antagonist, or administered to the subject as a single combined dosage formulation comprising both the additional therapeutic agent and the IL-4R antagonist.

In some embodiments, the additional therapeutic agent is a steroid, an antihistamine, a decongestant, or an anti-IgE agent. In some embodiments, the additional therapeutic agent is a steroid (e.g., a corticosteroid, such as an inhaled corticosteroid (ICS)). In some embodiments, the additional therapeutic agent is an antihistamine (e.g., loratadine, fexofenadine, cetirizine, diphenhydramine, promethazine, carbinoxamine, desloratadine, hydroxyzine, levocetirizine, triprolidine, brompheniramine, or chlorpheniramine). In some embodiments, the additional therapeutic agent is a decongestant (e.g., pseudoephedrine or phenylephrine). In some embodiments, the additional therapeutic agent is an anti-IgE agent (e.g., omalizumab).

EXAMPLES

The following examples are put forth so as to provide those of ordinary skill in the art with a complete disclosure and description of how to make and use the methods and compositions of the disclosure, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Clinical Trial Investigating the Efficacy of Dupilumab as an Adjunct for Subcutaneous Grass Immunotherapy Study Design and Objectives This was a Phase 2a, multicenter, randomized, double-blind, parallel group, 4-arm study of dupilumab as an adjunct to grass SCIT in adult subjects with a history of allergic rhinitis, conducted outside of Timothy Grass allergy season. Dupilumab is a fully human anti-IL-4R antibody comprising a heavy chain comprising the amino acid sequence of SEQ ID NO:9 and a light chain comprising the amino acid sequence of SEQ ID NO:10; an HCVR/LCVR amino acid sequence pair comprising SEQ ID NOs:1/2; and heavy and light chain CDR sequences comprising SEQ ID NOs:3-8.

Eligible patients with a history of allergic rhinitis to grass pollen who successfully complete screening procedures were randomized 1:1:1:1 into the 4 treatment arms as follows:

(1) SCIT up-titrated as described up to a 4,000 BAU maintenance dose+dupilumab (SC 300 mg Q2W, after 600 mg loading dose)
(2) SCIT up-titrated as described up to a 4,000 BAU maintenance dose+placebo for dupilumab
(3) Placebo for SCIT plus dupilumab (SC 300 mg Q2W, after 600 mg loading dose)
(4) Placebo for SCIT plus placebo for dupilumab Dupilumab was dosed as follows: Subjects are given a loading dose of 600 mg dupilumab subcutaneous (SC) or placebo on day 1, followed 2 weeks later by 300 mg Q2W SC, and continuing at 300 mg Q2W SC for a total of 16 weeks.

SCIT was dosed as follows: On the day following dupilumab dosing (up to 7 days after dupilumab loading dose), subjects begin an up-titration regimen of Timothy Grass SCIT beginning at 1 bioequivalent allergy unit (BAU) up to 4,000 BAU, in a modified cluster regimen over 8 weeks, and then maintained on 4,000 BAU for the remaining 8 weeks. If subjects develop side effects during the up-dosing phase of SCIT, the principal investigator (PI), in consultation with the medical monitor, may decide to reduce the planned maintenance dose of SCIT of 4000 BAU down to between 400 BAU and 4000 BAU but no lower than 400 BAU. Placebo matching SCIT is prepared in the same formulation (SCIT diluent) without the addition of Timothy Grass extract. All SCIT visits were supervised in an in-clinic study site setting where trained study physicians were present. Subjects were observed for at least 30 minutes after any SCIT injection. Standing orders from a study physician will be provided for all clinical study personnel to immediately initiate treatment of reactions, including but not limited to intramuscular administration of epinephrine, based on their own clinical judgment. For all SCIT visits subjects were pre-medicated with an H1 anti-histamine (loratadine 10 mg orally) 1-6 hours prior to each injection visit, as recommended by clinical guidelines to reduce local and systemic reactions during the cluster SCIT.

Screening

After obtaining informed consent, subjects were assessed for eligibility during a 3-part screening period as follows. During screening visit 1, subjects with a history of allergic rhinitis to grass pollen undergo a medical history, physical examination, SPT for Timothy Grass, and blood draw for Timothy Grass specific IgE. If the subject meets criteria with a positive SPT for Timothy Grass and for Timothy Grass specific IgE as per Inclusion/Exclusion criteria, they will be invited for screening visit 2. At screening visit 2 subjects undergo a pregnancy test if applicable, spirometry, electrocardiogram (ECG), serologic testing for chronic viral infections (Human Immunodeficiency Virus Infection [HIV] and Hepatitis B and C), hematology, chemistry, urinalysis, will be evaluated for the study eligibility criteria, and will undergo a baseline nasal brushing. The baseline nasal brushing must occur while TNSS ≤2 and it must be at least 28 days prior to the screening visit 3/Entry visit, so that the nasal mucosa may re-epithelialize and return to a resting state prior to NAC. At screening visit 3/Entry visit (day-1), subjects may not have taken anti-histamines for at least 5 days. If the subject reports having taken anti-histamines within 5 days of Screening visit 3, they can be rescheduled for Screening visit 3. At screening visit 3/Entry visit, subjects are observed for approximately 10 minutes and a resting/baseline TNSS ≤2 must be achieved, signifying that the subject does not have active nasal symptoms at rest (due to viral infection, sinusitis, allergies, etc.), prior to NAC. If the subject has a TNSS >2, signifying that they have active nasal symptoms at rest, they can be rescheduled for Screening visit 3. TNSS (measured on a 0-12 scale) is a composite symptom assessment of congestion, itching, rhinorrhea (each graded on 0-3 scale, 3 being severe), and sneezing (2 being 3-4 sneezes and 3 being >5 sneezes).

If the subject had a resting/baseline TNSS ≤2 and therefore had no appreciable nasal symptoms at rest, a NAC and skin testing for early and late phase reactions were performed as follows:

NAC is performed using increasing doses of Timothy Grass extract every 10 minutes up to 1 hour (up-titration phase), or until a TNSS ≥7 is reached.

The peak TNSS is recorded.

The Timothy Grass extract concentration that was used to attain TNSS ≥7 is recorded.

Subjects are observed for the subsequent hour and the TNSS is recorded at 5 minutes, 15 minutes, 30 minutes, 45 minutes, 1 hour, and then hourly up to 6 hours.

In addition to TNSS, the following parameters are measured at baseline, approximately every 10 minutes during the up-titration phase, and during the subsequent hour after peak TNSS is achieved (at 5 minutes, 15 minutes, 30 minutes, 45 minutes, and 1 hour) and hourly up to 6 hours:

PNIF; (measured in nasal patency, L/min)

Total sneezes

TOSS

Grass allergic subjects were eligible for enrollment based on having a TNSS ≤2 prior to the screening NAC (time 0), peak TNSS ≥7 within the first hour during the up-titration phase. Additionally for eligibility, between the first non-zero dose of and approximately 10 minutes after the highest/peak dose, subjects must have experienced either a >20% drop in PNIF or >/=3 sneezes must be counted.

Patient Selection

The target population included adults with a history of grass pollen-induced seasonal allergic rhinitis. The subjects were randomized at sites in North America in geographies where Timothy Grass is the relevant grass species.

Inclusion Criteria: A patient had to meet the following criteria to be eligible for inclusion in the study: (1) male or female, aged 18 to 55; (2) history of grass pollen-induced seasonal allergic rhinitis; (3) grass pollen allergy confirmed by both (a) positive SPT with Timothy Grass extract (mean wheal diameter at least mm greater than a negative control), and (b) positive serum Timothy Grass-specific IgE (≥0.35KU/L); (4) positive NAC with Timothy Grass extract at screening with peak TNSS score ≥7 out of 12; (5) between the first non-zero dose and approximately 10 minutes after the highest dose of NAC, participants must experience either a >20% drop in PNIF or ≥3 sneezes must be counted; (6) provide informed consent signed by study subject; (7) able to understand and complete study-related questionnaires; and (8) willing and able to comply with study site visits and study-related procedures.

Exclusion Criteria: The following were exclusion criteria for the study: (1) significant rhinitis (causing TNSS >2), sinusitis, outside of the grass pollen season, or due to daily contact with other allergens causing symptoms that is expected to coincide with the baseline or the final NAC assessments as assessed by the investigator; (2) subjects who anticipate major changes in allergen exposure in their home or work environments that are expected to coincide with the baseline or the final NAC assessments as assessed by the investigator; (3) at screening NAC, current symptoms of, or treatment for, upper respiratory tract infection, acute sinusitis, acute otitis media, or other relevant infectious process; serous otitis media is not an exclusion criterion [Participants may be re-evaluated for eligibility after symptoms resolve]; (4) any contraindications to SCIT (i.e., severe cardiovascular disease, malignancies, autoimmune disease, use of beta blocker, asthma severe enough to require chronic medication, acute infection); (5) patients with any laboratory findings showing evidence of organ dysfunction or any clinically significant deviation from the normal range, as decided by the investigator at the screening visit, including but not limited to: clinically significant/active underlying hepatobiliary disease, or alanine aminotransferase (ALT) >3 upper limit of normal (ULN); and abnormal laboratory values at screening: creatine phosphokinase (CPK) >10 ULN, or platelets <100 000 cells/mm$^3$, or eosinophils >1500 cells/mm$^3$; (6) use of any concomitant medications within the following time period preceding any screening visit or any screening NAC visit (Visit 3) including antihistamines (5 days), leukotriene inhibitors (7 days), mast cell inhibitors (7 days), intranasal corticosteroids and/or inhaled corticosteroids (14 days), oral or topical decongestants (5 days), topical calcineurin inhibitors (4 weeks), beta blockers (5 days) [Participants may be re-evaluated for eligibility after the time period for taking these concomitant medications has passed]; (7) use of systemic corticosteroids within 4 weeks of screening visits or any NAC visits; (8) abnormal lung function as judged by the investigator with $FEV_1$ <80% of predicted; (9) a clinical history of asthma requiring chronic medication such as regular inhaled corticosteroids for >4 weeks per year; (10) clinical history of asthma with 2 or more asthma exacerbations requiring hospitalizations or systemic corticosteroids in the previous year; (11) history of emergency visit or hospital admission for asthma in the previous 12 months; (12) history of significant recurrent sinusitis, defined as 3 episodes per year for the last 2 years, all of which required antibiotic treatment; (13) history of chronic sinusitis (with or without nasal polyps) as defined as: presence of two or more symptoms one of which should be either nasal blockage/obstruction/congestion or nasal discharge (anterior/posterior nasal drip): ± facial pain/pressure; ± reduction or loss of smell; for ≥12 weeks; (14) any gross mechanical nasal obstruction, or history of nasal or sinus surgery that would interfere with the conduct of the NAC, as per judgment of the investigator; (15) tobacco smoking (ANY) within the last year; (16) any history of grade 4 anaphylaxis due to any cause as defined by the Common Terminology Criteria for Adverse Events (CTCAE) grading criteria for immunotherapy; (17) history of chronic obstructive pulmonary disease; (18) history of other chronic disease (other than asthma, atopic dermatitis, allergic rhinitis) requiring therapy (e.g., heart disease, diabetes, hypertension) that, in the opinion of the investigator, would represent a risk to the subject's health or safety in this study or the subject's ability to comply with the study protocol; (19) history of previous allergy immunotherapy (SCIT, sublingual immunotherapy, or oral immunotherapy) in the last 5 years; (2) any previous exposure to dupilumab; (21) treatment with an investigational drug within 2 months or within 5 half-lives (if known), whichever is longer, prior to screening; (22) member of the clinical site study team or his/her immediate family; (23) known or suspected immunosuppression, including history of invasive opportunistic infections (e.g., tuberculosis, histoplasmosis, listeriosis, coccidioidomycosis, pneumocystosis, aspergillosis) despite infection resolution, or otherwise recurrent infections of abnormal frequency, or prolonged infections suggesting an immune compromised status, as judged by the investigator; (24) history of patient-reported alcohol or drug abuse within 6 months prior to screening; (25) history of bleeding disorders or treatment with anticoagulation therapy; (26) subjects tested positive for HIV antibody, Hepatitis B surface antigen, or Hepatitis C antibody; (27) use of anti-IgE therapy within 6 months prior to screening; (28) treatment with a live (attenuated) vaccine within 3 months prior to screening and during the study; (29) active chronic or acute infection requiring systemic treatment with antibiotics, antivirals, antiparasitics, antiprotozoals, or antifungals within 2 weeks prior to the screening visit [NOTE: subjects may be rescreened after the infection resolves]; (30) history of malignancy within 5 years before the screening visit, except completely treated in situ carcinoma of the cervix, completely treated and resolved non-metastatic squamous or basal cell carcinoma of the skin; (31) established diagnosis of a primary immunodeficiency disorder (e.g., Severe Combined Immunodeficiency, Wiskott Aldrich Syndrome, DiGeorge Syndrome, X-linked Agammaglobulinemia, Common Variable Immunodeficiency), or secondary immunodeficiency e.g., HIV; (32) pregnant or breastfeeding women, women planning to become pregnant or breastfeed during the study; (33) women of child bearing potential* who are not sexually abstinent and are unwilling to practice highly effective contraception prior to the initial dose/start of the first treatment, during the study, and for at least 120 days after the last dose [*Postmenopausal women must be amenorrheic for at least 12 months in order not to be considered of childbearing potential. Pregnancy testing and contraception are not required for women with documented hysterectomy or tubal ligation]. Highly effective contraceptive measures include: (a) a. stable use of combined (estrogen and progestogen containing) hormonal contraception (oral, intravaginal, transdermal) or progestogen-only hormonal contraception (oral, injectable, implantable) associated with inhibition of ovulation initiated 2 or more menstrual cycles prior to screening; (b) intrauterine device (IUD); intrauterine hormone releasing system (IUS); (c) bilateral tubal ligation; (d) vasectomized partner; and/or (e) sexual abstinence †, ‡[†Sexual abstinence is considered a highly effective method only if defined as refraining from heterosexual intercourse during the entire period of risk associated with the study treatments. The reliability of sexual abstinence needs to be evaluated in relation to the duration of the clinical trial and the preferred and usual lifestyle of the subject. ‡periodic abstinence (calendar, symptothermal, post-ovulation methods), withdrawal (coitus interruptus), spermicides only, and lactational amenorrhoea method (LAM) are not acceptable methods of contraception. Female condom and male condom should not be used together.] (34) subjects unable to understand and comply with clinical protocol; (35) planned or anticipated use of any prohibited medications and procedures during study treatment; and (36) adults lacking capacity to consent themselves into the study.

Study Treatments

Dupilumab: Patients received a loading dose of 600 mg dupilumab SC or placebo, followed by 300 mg Q2W SC for a total of 16 weeks.

Timothy Grass SCIT: Timothy Grass SCIT was given using cluster dose escalation regimen over 8 weeks then maintenance therapy was given, as described below. SCIT was started no earlier than 1 day after the dupilumab loading dose and up to 1 week after the dupilumab loading dose. Dosing of dupilumab was not performed on the same day and administration site as SCIT.

The Grass SCIT protocol comprises 1-3 SC injections per week visit of allergen following the up-titration regimen described below over 8 weeks followed by the maintenance SC injections for the following 8 weeks as shown in Table 1 below. The recommended target maintenance dose for SCIT is 4,000 bioequivalent allergy units (BAU), which is equivalent to approximately 20 mcg Phlem Pratense 5 (major Timothy Grass allergen) (Cox, 2011) (Frew, 2006b). During weeks 1-3 of the up-dosing phase, 3 doses of SCIT were given per visit: the first (lowest dose for that visit) was given, the subject was monitored for 30 minutes, and if the dose was well tolerated, the next higher scheduled dose for that visit was given. The subject was then monitored for the next 30 minutes, and if the dose was well tolerated, the next higher scheduled dose for that visit was given. During weeks 4-5 of the up-dosing phase, 2 doses of SCIT were given: the first (lowest dose for that visit) was given, subject was monitored for 30 minutes, and if the dose was well tolerated, the next higher scheduled dose for that visit was given. During weeks 6-8 of the up-dosing phase, 1 dose of SCIT was given. During the maintenance phase, one dose was given per visit as per Table 1. Placebo SCIT was given in the same manner as the Grass SCIT, following the same protocol, but instead of active agent, diluent was given. The first (lowest dose for that visit) was given, the subject was monitored for 30 minutes, and if the dose was well tolerated, the next higher scheduled dose for that visit was given. On days when SCIT or placebo SCIT were given, subjects were pre-medicated with an H1 anti-histamine (loratadine 10 mg orally) 1-6 hours prior to each injection visit, as recommended by clinical guidelines to reduce local and systemic reactions during cluster SCIT.

TABLE 1

SCIT Up-Titration and Maintenance Regimen

| Week No. | Injection No. | Subcutaneous Dose of SCIT (BAU) |
|---|---|---|
| 1 | 1 | 1 |
| 1 | 2 | 4 |
| 1 | 3 | 10 |
| 2 | 4 | 20 |
| 2 | 5 | 40 |
| 2 | 6 | 70 |
| 3 | 7 | 100 |
| 3 | 8 | 150 |
| 3 | 9 | 250 |
| 4 | 10 | 400 |
| 4 | 11 | 700 |
| 5 | 12 | 1000 |
| 5 | 13 | 1500 |
| 6 | 14 | 2000 |
| 7 | 15 | 3000 |
| 8 | 16 | 4000 |
| 10 | 17 | 4000 |
| 13 | 18 | 4000 |
| 16 | 19 | 4000 |

Timing of Dupilumab/Placebo and SCIT/Placebo

Dupilumab dosing started prior to SCIT dosing as shown in Table 2. Dupilumab/placebo are never to be given on the same day as SCIT/placebo.

TABLE 2

Dosing Schedule for Dupilumab/Placebo with Respect to SCIT/Placebo

| Dose | Dupilumab/Placebo[1] | SCIT/Placebo |
|---|---|---|
| NAC | | |
| Randomization (V4) | $X^2$ | |
| Week 1 | | $X^{3,5}$ |
| Week 2 | $X^4$ | $X^5$ |
| Week 3 | | $X^{4,5}$ |
| Week 4 | $X^4$ | $X^5$ |
| Week 5 | | $X^{4,5}$ |
| Week 6 | $X^4$ | $X^5$ |
| Week 7 | | $X^{4,5}$ |
| Week 8 | $X^4$ | $X^5$ |
| Week 9 | | |
| Week 10 | $X^4$ | $X^5$ |

TABLE 2-continued

Dosing Schedule for Dupilumab/Placebo with Respect to SCIT/Placebo

| Dose | Dupilumab/Placebo[1] | SCIT/Placebo |
|---|---|---|
| Week 11 | | |
| Week 12 | $X^4$ | |
| Week 13 | | $X^{4,5}$ |
| Week 14 | $X^4$ | |
| Week 15 | | |
| Week 16 | $X^4$ | $X^5$ |
| NAC | | |

[1]Dupilumab/placebo dosing given ±3 days of the visit window.
[2]Dupilumab or placebo for dupilumab loading dose given day of randomization. Subsequent dupilumab/placebo dosing given Q2W
[3]SCIT/placebo given 1 to 7 days following dupilumab/dupilumab placebo loading dose. Subsequent SCIT/placebo dosing follows dosing regimen as depicted in Table 1.
[4]During week 2, week 4, week 6, week 10, and week 16, when both dupilumab/placebo and SCIT/placebo were given in the same week, SCIT/placebo and dupilumab/placebo were not given on the same day (can be 1 day to 7 days apart) AND SCIT/placebo and dupilumab/placebo were given in a different anatomical location.
[5]For SCIT/placebo visits, subjects premedicated with an antihistamine.

Rescue Treatments

If required, subjects who experienced allergic reactions were treated with rescue treatment including but not limited to IM or SC administration of epinephrine, as determined by trained study staff. Subjects may also take oral antihistamines as needed for allergic rhinitis symptoms during the course of the study, however oral antihistamines may not be used within 5 days prior to or during a visit for NAC or skin testing. If subject uses oral antihistamines within 5 days prior to or during a visit for NAC or skin testing they must be rescheduled.

Procedures and Assessments

A variety of parameters was collected during the study to assess the efficacy/effectiveness of dupilumab monotherapy, SCIT monotherapy, dupilumab+SCIT, and placebo. These parameters included NAC and NAC assessments (TNSS, TOSS, PNIF, and total sneezes) and biomarker analysis (TARC, total IgE, Timothy Grass specific IgE, Timothy Grass specific IgG4) in serum or plasma.

NAC and NAC Assessments (TNSS, TOSS, PNIF, and Total Sneezes)

TNSS: TNSS assessment was performed as follows: At the end of treatment NAC (week 17), subjects will be observed for approximately 10 minutes and a resting/baseline TNSS ≤2 must be achieved, signifying that the subject does not have active nasal symptoms at rest (due to viral infection, sinusitis, allergies, etc.), prior to NAC. TNSS (measured on a 0-12 scale) is a composite symptom assessment of congestion, itching, rhinorrhea (each graded on 0-3 scale, 3 being severe), and sneezing (2 being 3-4 sneezes and 3 being >5 sneezes. If the subject has a resting/baseline TNSS ≤2 and therefore has no appreciable nasal symptoms at rest, a NAC will be performed. The NAC will be performed using increasing doses of Timothy Grass extract every 10 min, with TNSS score recorded approximately every 10 minutes (up-titration symptom score), up until they reach the concentration of Timothy Grass extract that was used to achieve a Total Nasal Symptom Score (TNSS) ≥7 at their baseline NAC visit. This TNSS score will be recorded. After recording the TNSS attained using concentration of Timothy Grass extract that was used to achieve a Total Nasal Symptom Score (TNSS) ≥7 at their baseline NAC visit, the subject will be observed for the subsequent hour and the TNSS will be recorded at 5 minutes, 15 minutes, 30 minutes, 45 minutes, 1 hour, and then hourly up to 6 hours.

TOSS: TOSS (measured on a 0-3 scale, 3 being severe) is a composite symptom assessment of ocular symptoms (Itchy, Red, tearing [eyes watering], and swelling [puffy eyes] that was assessed as follows: The TOSS score will be recorded during the NAC assessments. The TOSS score will be recorded approximately every 10 minutes (up-titration symptom score), up until they reach the concentration of Timothy Grass extract that was used to achieve a TNSS ≥7 at their baseline NAC visit. This TOSS score will be recorded. The subject will be observed for the subsequent hour and the TOSS score will be recorded at 5 minutes, 15 minutes, 30 minutes, 45 minutes, 1 hour, and then hourly up to and at 6 hours.

PNIF: PNIF assessment was performed as follows: Peak nasal inspiratory flow (measured in nasal patency, L/min) will be measured and recorded approximately every 10 minutes during the up-titration phase of the NAC and will be measured and recorded during the subsequent hour after peak TNSS is achieved (at 5 minutes, 15 minutes, 30 minutes, 45 minutes, and 1 hour) and hourly up to and at 6 hours.

Total sneezes: Total sneezes were counted and recorded during the up-titration phase and during the hour after peak TNSS is achieved.

Additionally, skin prick test (SPT) with serial allergen titration was performed to assess the early phase reaction at 0-60 minutes. Intradermal allergen injection was performed to assess late phase reaction from 6-24 hours. Nasal fluid was collected during the 2 NAC study visits to determine the levels of cytokines and chemokines produced in response to NAC. The safety of dupilumab in this population was assessed by evaluating AEs, detailed medical history, thorough physical examination, vital signs, electrocardiogram (ECG), spirometry, peak expiratory flow, and clinical laboratory testing. Concomitant medications and procedures were collected from time of informed consent to the end of the study. Blood samples were collected for drug concentration and anti-dupilumab antibody levels at pre-determined time points. Research samples and samples for exploratory biomarker analysis were collected.

Pharmacokinetic and Biomarker Procedures

Biomarkers: Biomarker samples were collected at specified timepoints. Biomarker measurements (TARC, total IgE, Timothy Grass specific IgE, Timothy Grass specific IgG4) were performed in serum or plasma to determine effects on biomarkers of relevant physiological and pathogenic processes.

Pharmacokinetics: Concentration data was determined at each sampling time.

Statistical Analyses

Primary and continuous secondary efficacy endpoints were analyzed by using the multiple imputation (MI) with analysis of covariance (ANCOVA) model and last observation carry forward (LOCF) method. For MI, missing data were imputed 40 times to generate 40 complete data sets by using the Statistical Analysis System (SAS) procedure MI. Each of the 40 complete datasets were analyzed using an ANCOVA model with treatment group being the main factor and baseline value as the covariate. The SAS MIANALYZE procedure was used to generate valid statistical inferences by combining results from the 40 analyses using Rubin's formula. All observed data was used for analysis.

The biomarker related continuous endpoint was analyzed using a rank based ANCOVA model with treatment and relevant baseline as covariates. LOCF method was used to impute the missing data.

Results

Patient Baseline Characteristics 103 patients were randomized to placebo (n=25) or to one of three treatment arms: dupilumab (n=26), SCIT (n=26), or dupilumab+SCIT (n=26). Baseline demographics and clinical characteristics were relatively balanced between the treatment groups (Table 3).

TABLE 3

Baseline Demographics

|  | Placebo (N = 25) | Dupi (N = 26) | SCIT (N = 26) | Dupi + SCIT (N = 26) |
| --- | --- | --- | --- | --- |
| Male, n (%) | 15 (60.0%) | 10 (38.5%) | 12 (46.2%) | 16 (61.5%) |
| Age (yrs), mean (min, max) | 35 (20, 53) | 40 (21, 53) | 38 (18, 54) | 33 (18, 55) |
| Screening grass SPT Wheal Diameter (mm) AUC, mean (min, max) | 14 (5.8, 23.1) | 11 (5.2, 23.5) | 13 (6.6, 22.0) | 14 (6.4, 28.1) |
| Screening grass sIgE (kU/L), mean (min, max) | 27 (0.50, 230.00) | 16 (0.59, 174.00) | 19 (0.57, 35.00) | 44 (0.74, 644.00) |
| Screening NAC TNSS qualifying peak score, mean (min, max) | 9.2 (7, 12) | 8.5 (7, 12) | 8.3 (7, 11) | 8.7 (7, 12) |
| Asthma, n (%) | 9 (36.0%) | 7 (26.9%) | 9 (34.6%) | 10 (38.5%) |

Safety

In a 16-week regimen of SCIT, significantly more patients in the group that was treated with SCIT alone discontinued therapy, due to clinically significant SCIT-related allergic reactions. 8 of 26 (31%) patients in the SCIT treatment group discontinued during the 16-week SCIT treatment phase (7/8 due to clinically significant SCIT-related allergic reactions), while only 1 of 26 (4%) of patients in the dupilumab +SCIT treatment group discontinued SCIT treatment; this patient's discontinuation was not related to a SCIT reaction.

Table 4 shows that treatment with dupilumab in combination with SCIT reduced the need for use of epinephrine and oral steroids to treat systemic reactions, as compared to the SCIT group. For the SCIT group, 19.2% of subjects required epinephrine (compared to 7.7% for the dupilumab+SCIT group) and 19.2% of subjects required oral steroids (compared to 7.7% for the dupilumab+SCIT group). A higher number of systemic allergic reactions after SCIT injection were observed for the dupilumab+SCIT group (11, vs. 10 for the SCIT group, 1 for the dupilumab group, and 1 for the placebo group; of the 11 reactions, 2 were Grade 1 and 9 were Grade 2; none were Grade 3, in contrast to the SCIT group, which had 2 Grade 3 systemic allergic reactions). Adverse events and serious adverse events were similar across treatment groups. There were two serious adverse events in the dupilumab+SCIT group, and 1 each for each of the SCIT, dupilumab, and placebo groups.

TABLE 4

Safety Results

| % of Subjects with, n (%) | Placebo (N = 25) | Dupi (N = 26) | SCIT (N = 26) | Dupi + SCIT (N = 26) |
|---|---|---|---|---|
| Death | 0 | 0 | 0 | 0 |
| TEAE | 21 (84.0%) | 18 (69.2%) | 24 (92.3%) | 22 (84.6%) |
| SAE | 1 (4.0%) | 1 (3.8%) | 1 (3.8%) | 2 (7.7%) |
| TEAE leading to discontinuation of study drug (dupi or SCIT) | 0 | 2 (7.7%) | 5 (19.2%) | 1 (3.8%) |
| TEAE leading to discontinuation of dupi | 0 | 2 (7.7%) | 4 (15.4%) | 1 (3.8%) |
| TEAE leading to discontinuation of SCIT | 0 | 1 (3.8%) | 5 (19.2%) | 1 (3.8%) |
| TEAE of Special Interest (Adjudicated) | 1 (4.0%) | 2 (7.7%) | 7 (26.9%) | 11 (42.3%) |
| Anaphylactic reactions | 0 | 1 (3.8%) | 2 (7.7%) | 1 (3.8%) |
| Systemic or severe hypersensitivity reactions | 1 (4.0%) | 1 (3.8%) | 7 (26.9%) | 11 (42.3%) |
| Keratitis | 0 | 0 | 0 | 1 (3.8%) |
| Malignancy | 0 | 1 (3.8%) | 0 | 0 |
| Systemic allergic reaction after SCIT injection | 1 (4.0%) | 1 (3.8%) | 10 (38.5%) | 11 (42.3%) |
| Grade 1 | 1 (4.0%) | 1 (3.8%) | 3 (11.5%) | 2 (7.7%) |
| Grade 2 | 0 | 0 | 5 (19.2%) | 9 (34.6%) |
| Grade 3 | 0 | 0 | 2 (7.7%) | 0 |
| Rescue medications for allergic reaction to SCIT | 0 | 2 (7.7%) | 14 (53.8%) | 14 (53.8%) |
| Epinephrine | 0 | 1 (3.8%) | 5 (19.2%) | 2 (7.7%) |
| Oral antihistamine | 0 | 2 (7.7%) | 12 (46.2%) | 12 (46.2%) |
| Oral steroid | 0 | 0 | 5 (19.2%) | 2 (7.7%) |
| Topical steroid | 0 | 0 | 2 (7.7%) | 1 (3.8%) |
| SABA | 0 | 0 | 2 (7.7%) | 4 (15.4%) |
| SCIT injection site reaction | 9 (36%) | 6 (23.1%) | 20 (76.9%) | 19 (73.1%) |
| Number of SCIT injection site reaction | 49 | 41 | 220 | 399 |
| Treatment duration (days), mean (SD) | 127.3 (5.22) | 123.2 (15.04) | 102.1 (42.18) | 125.5 (14.07) |

Efficacy

LOCF analysis of the primary endpoint, as measured by percent change in TNSS AUC (0 hour to hour 1) after NAC, suggested a benefit from administering dupilumab as an adjunct to SCIT. LOCF analysis considered the discontinued patients in the treatment groups to be "non-responders" and assigned a Total Nasal Symptom Score (TNSS) after allergen-challenge of "0 change from baseline." As shown in Table 5, treatment with SCIT alone resulted in a placebo-corrected reduction in TNSS of −16.3% (p=0.1871), while dupilumab+SCIT resulted in a placebo-corrected reduction in TNSS of −24.6% (p=0.0474).

inhibit sIgE during the SCIT maintenance phase. Both SCIT and dupilumab+SCIT increased serum Timothy Grass sIgG4 to a similar magnitude and with similar kinetics (1896% for dupilumab+SCIT vs 1812% for SCIT). Treatment with dupilumab in combination with SCIT increased the ratio [log] of sIgG4/sIgE at week 17 as compared to treatment with SCIT alone (1.7 vs 0.87, p<0.0001). Both SCIT and dupilumab+SCIT also increased specific total IgG over 16 weeks. Patients treated with dupilumab, or with dupilumab in combination with SCIT, exhibited reduced systemic TARC levels at week 17, as compared to the placebo and SCIT groups.

TABLE 5

Efficacy Results

| Parameters | Placebo (PBO) (N = 25) | Dupi (N = 26) | SCIT (N = 26) | Dupi + SCIT (N = 26) | Diff SCIT vs PBO | Diff Dupi + SCIT vs PBO |
|---|---|---|---|---|---|---|
| % Change in TNSS AUC (LOCF*) LSmean(SE) (95% CI) p-value | −27.6 (8.74) (−45.00, −10.30) | −18.4 (8.53) (−35.34, −1.48) | −43.9 (8.55) (−60.91, −26.99) | −52.3 (8.54) (−69.23, −35.32) | −16.3 (−40.64, 8.05) P = 0.1871 | −24.6 (−48.96, −0.29) P = 0.0474 |

Biomarkers

The results of biomarker analysis are shown in Table 6. SCIT significantly increased the amount of serum Timothy Grass sIgE from baseline (an increase of 98% at week 17). It was also observed that individuals with a dramatic increase in IgE had an increased risk of discontinuation. The addition of dupilumab to SCIT inhibited the rise in grass specific IgE (56.4% reduction); dupilumab inhibited the rise in sIgE very early during SCIT up-dosing and continued to In completers (not corrected for non-responders), skin prick testing with serial allergen titration showed similar results for SCIT and dupilumab in combination with SCIT (−45.2% change in wheal size for SCIT vs −47.1% for dupilumab+SCIT). Skin prick testing induced by intradermal allergen injection showed a greater decrease for SCIT as compared to dupilumab in combination with SCIT (−42.4% vs −10.7%).

TABLE 6

Biomarker Measurements from Baseline to Week 16

| Parameters | Placebo (N = 25) | Dupi (N = 26) | SCIT (N = 26) | Dupi + SCIT (N = 26) |
|---|---|---|---|---|
| % Change in sIgE (LOCF) Median, Median diff (95% CI), p-value | −37.2 | −16.9 | 98 | −56.4 |
| Change in sIgE (LOCF) Median, Median diff (95% CI), p-value | −1.11 | −0.585 | 6.76 | −2.99 |
| % Change in sIgG4 (LOCF) Median, Median diff (95% CI), p-value | 19 | 0 | 1812.5 | 1896.3 |
| Change in sIgG4 (LOCF) Median, Median diff (95% CI), p-value | 0.05 | 0 | 1.92 | 3.55 |
| Change in log (sIgG4/sIgE) (LOCF) Median, Median diff (95% CI), p-value | 0.31 | 0.235 | 0.865 | 1.72 |
| % Change in TARC (LOCF) Median, Median diff (95% CI), p-value | 7.1 | −28.7 | 1 | −25.5 |
| Change in TARC (LOCF) Median, Median diff (95% CI), p-value | 21 | −71 | 2 | −62 |
| % Change in sIgG (LOCF) Median, Median diff (95% CI), p-value | 0 | 0 | 242.4 | 454.6 |
| Change in sIgG (LOCF) Median, Median diff (95% CI), p-value | 0 | 0 | 6.35 | 10.35 |
| % Change in IgE (LOCF) Median, Median diff (95% CI), p-value | −8.4 | −30.9 | 48.3 | −33.2 |
| Change in IgE (LOCF) Median, Median diff (95% CI), p-value | −4.7 | −31.35 | 42.15 | −39.25 |
| Change in log (sIgG/sIgE) (LOCF) Median, Median diff (95% CI), p-value | 0.19 | 0.13 | 0.265 | 1.105 |

Pharmacokinetics

Concentrations of functional dupilumab were similar in the presence or absence of SCIT treatment. Mean and median values, as well as variability, of functional dupilumab concentration were consistent between the dupilumab+SCIT and dupilumab groups. Functional dupilumab concentrations appear to be at steady state by week 5 as $C_{trough}$ measurements appeared consistent from week 5 to week 17 for both groups. Following the end of treatment (week 17), mean functional dupilumab concentrations declined from approximately 79 mg/L to 16 mg/L at week 24 for both groups.

Tolerability

Data for tolerability parameters (percentage of subjects achieving a SCIT of 4000 BAU by week 8 or week 16 and maximum tolerated dose by week 8 or week 16) are shown in Table 7. Treatment with dupilumab in combination with SCIT increased the number of subjects who successfully achieved 16 weeks of SCIT dosing as compared to the SCIT group (92% vs 69%). Treatment with dupilumab in combination with SCIT also increased the number of subjects who achieved the maintenance dose of 4000 BAU (full up-titration) (62% vs 46%). A higher mean SCIT dose was achieved in the dupilumab+SCIT group vs the SCIT group after 16 weeks (3071 BAU vs 2683 BAU).

CONCLUSION

In this Phase 2a clinical trial, administration of dupilumab as an adjunct to SCIT resulted in a marked improvement in safety and tolerability as compared to SCIT alone. Treatment with dupilumab improved the tolerability of SCIT as measured by the percentage of patients who completed 16 weeks of SCIT dosing, the percentage of patients who achieved full maintenance dose, the mean SCIT dose achieved at 16 weeks, and the decreased need for epinephrine and oral steroids as rescue medications.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

TABLE 7

Tolerability Results

| Parameters | SCIT (N = 26) | Dupi + SCIT (N = 26) |
|---|---|---|
| % Subject Achieving SCIT 4000 BAU by week 8, n (%) (95% CI) p-value | 9 (34.6%) (16.3, 52.9) | 14 (53.8%) (34.7, 73.0) |
| % Subject Achieving SCIT 4000 BAU by week 16, n (%) (95% CI) p-value | 12 (46.2%) (27.0, 65.3) | 16 (61.5%) (42.8, 80.2) |
| SCIT max tolerance dose by week 8, mean (SD) median, p-value | 1819.4 (1712.64) 1250.0 | 2682.7 (1537.20) 4000.0 |
| SCIT max tolerance dose by week 16, mean (SD) median, p-value | 2246.3 (1753.44) 2000.0 | 3071.2 (1330.13) 4000.00 |

What is claimed is:

1. A method for enhancing the efficacy and/or tolerability of a grass allergen-specific subcutaneous immunotherapy (SCIT) regimen in a subject having a grass allergy, the method comprising administering to the subject one or more doses of an interleukin-4 receptor (IL-4R) antagonist in combination with the SCIT regimen, wherein at least one dose of the IL-4R antagonist is administered prior to the start of the SCIT regimen, and wherein the IL-4R antagonist is an anti-IL-4R antibody, or an antigen-binding fragment thereof, that comprises the heavy chain complementarity determining regions (HCDRs) of a heavy chain variable region (HCVR) comprising the amino acid sequence of SEQ ID NO:1 and the light chain complementarity determining regions (LCDRs) of a light chain variable region (LCVR) comprising the amino acid sequence of SEQ ID NO:2.

2. The method of claim 1, wherein the SCIT regimen comprises subcutaneous administration of a grass extract that is from a grass selected from the group consisting of Timothy, Bahia, Bermuda, Johnson, Kentucky bluegrass, Orchard, Redtop, Rye, Sweet Vernal, Meadow Fescue, and combinations thereof.

3. The method of claim 2, wherein the grass extract is from Timothy grass.

4. The method of claim 1, wherein the SCIT regimen comprises a cluster SCIT regimen.

5. The method of claim 4, wherein the cluster SCIT regimen comprises an up-titration regimen followed by a maintenance regimen, wherein the up-titration regimen comprises administering increasing doses of the grass extract over a period of 4 to 12 weeks and wherein the maintenance regimen comprises administering one or more maintenance doses of the grass extract at the highest dose administered during the up-titration regimen.

6. The method of claim 5, wherein the up-titration regimen comprises administering increasing doses of the grass extract over a period of 8 weeks.

7. The method of claim 5, wherein the maintenance regimen comprises administering maintenance doses every 1 to 4 weeks for at least 8 weeks.

8. The method of claim 5, wherein the up-titration regimen comprises up-titrating from a dose of 1 bioequivalent allergy unit (BAU) to a dose of 4,000 BAU and wherein the maintenance regimen comprises administering one or more maintenance doses at 4,000 BAU.

9. The method of claim 1, wherein the IL-4R antagonist is administered at a dose of about 75 mg to about 600 mg.

10. The method of claim 1, wherein the IL-4R antagonist is administered as an initial dose followed by one or more secondary doses, wherein each secondary dose is administered 1 to 4 weeks after the immediately preceding dose.

11. The method of claim 10, wherein the initial dose of the IL-4R antagonist is administered from 1 to 7 days before the start of the SCIT regimen.

12. The method of claim 10, wherein the initial dose comprises 600 mg and each secondary dose comprises 300 mg of the IL-4R antagonist.

13. The method of claim 10, wherein each secondary dose is administered 2 weeks after the immediately preceding dose.

14. The method of claim 1, wherein the IL-4R antagonist and the SCIT are not administered to the subject on the same day.

15. The method of claim 1, wherein enhancing the efficacy and/or tolerability of the SCIT regimen comprises reducing allergic rhinitis symptoms in the subject.

16. The method of claim 1, wherein enhancing the efficacy and/or tolerability of the SCIT regimen comprises:
   (a) increasing the amount of serum grass allergen-specific IgG4 (sIgG4) in the subject relative to SCIT monotherapy;
   (b) decreasing the amount of serum grass allergen-specific IgE (sIgE) in the subject relative to SCIT monotherapy; and/or
   (c) increasing the ratio of sIgG4 to sIgE in the subject relative to SCIT monotherapy.

17. The method of claim 1, wherein administration of the IL-4R antagonist in combination with the SCIT regimen reduces or inhibits the induction of sIgE during the SCIT up-titration regimen and/or the SCIT maintenance regimen.

18. The method of claim 1, wherein administration of the IL-4R antagonist in combination with the SCIT regimen increases the maximum SCIT dose that is tolerated by the subject.

19. The method of claim 1, wherein administration of the IL-4R antagonist in combination with the SCIT regimen reduces the use of epinephrine or an oral steroid as a rescue medication.

20. The method of claim 1, wherein the anti-IL-4R antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO:3; the HCDR2 comprises the amino acid sequence of SEQ ID NO:4; the HCDR3 comprises the amino acid sequence of SEQ ID NO:5; the LCDR1 comprises the amino acid sequence of SEQ ID NO:6; the LCDR2 comprises the amino acid sequence of SEQ ID NO:7; and the LCDR3 comprises the amino acid sequence of SEQ ID NO:8.

21. The method of claim 1, wherein the anti-IL-4R antibody or antigen-binding fragment thereof comprises a HCVR comprising the amino acid sequence of SEQ ID NO:1 and comprises a LCVR comprising the amino acid sequence of SEQ ID NO:2.

22. The method of claim 1, wherein the anti-IL-4R antibody comprises a heavy chain comprising the amino acid sequence of SEQ ID NO:9 and a light chain comprising the amino acid sequence of SEQ ID NO:10.

23. The method of claim 1, wherein the IL-4R antagonist is dupilumab or a bioequivalent thereof.

24. The method of claim 1, wherein the IL-4R antagonist is contained in a container selected from the group consisting of a glass vial, a syringe, a pre-filled syringe, a pen delivery device, and an autoinjector.

25. The method of claim 24, wherein the IL-4R antagonist is contained in a pre-filled syringe.

26. The method of claim 25, wherein the pre-filled syringe is a single-dose pre-filled syringe.

27. The method of claim 24, wherein the IL-4R antagonist is contained in an autoinjector.

28. The method of claim 24, wherein the IL-4R antagonist is contained in a pen delivery device.

* * * * *

SEQUENCE LISTING

<160> NUMBER OF SEQ ID NOS: 11

<210> SEQ ID NO 1
<211> LENGTH: 124
<212> TYPE: PRT
<213> ORGANISM: Artificial Sequence
<220> FEATURE:
<223> OTHER INFORMATION: HCVR

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 2
<211> LENGTH: 112
<212> TYPE: PRT
<213> ORGANISM: Artificial Sequence
<220> FEATURE:
<223> OTHER INFORMATION: LCVR

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 3
<211> LENGTH: 8
<212> TYPE: PRT
<213> ORGANISM: Artificial Sequence
<220> FEATURE:
<223> OTHER INFORMATION: HCDR1

<400> SEQUENCE: 3

Gly Phe Thr Phe Arg Asp Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: HCDR2

<400> SEQUENCE: 4

Ile Ser Gly Ser Gly Gly Asn Thr
1               5

<210> SEQ ID NO 5
<211> LENGTH: 18
<212> TYPE: PRT
<213> ORGANISM: Artificial Sequence
<220> FEATURE:
<223> OTHER INFORMATION: HCDR3

<400> SEQUENCE: 5

Ala Lys Asp Arg Leu Ser Ile Thr Ile Arg Pro Arg Tyr Tyr Gly Leu
1               5                   10                  15

Asp Val

<210> SEQ ID NO 6
<211> LENGTH: 11
<212> TYPE: PRT
<213> ORGANISM: Artificial Sequence
<220> FEATURE:
<223> OTHER INFORMATION: LCDR1

<400> SEQUENCE: 6

Gln Ser Leu Leu Tyr Ser Ile Gly Tyr Asn Tyr
1               5                   10

<210> SEQ ID NO 7
<211> LENGTH: 3
<212> TYPE: PRT
<213> ORGANISM: Artificial Sequence
<220> FEATURE:
<223> OTHER INFORMATION: LCDR2

<400> SEQUENCE: 7

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: LCDR3

<400> SEQUENCE: 8

Met Gln Ala Leu Gln Thr Pro Tyr Thr
1               5

<210> SEQ ID NO 9
<211> LENGTH: 451
<212> TYPE: PRT
<213> ORGANISM: Artificial Sequence
<220> FEATURE:
<223> OTHER INFORMATION: HC

<400> SEQUENCE: 9

Glu Val Gln Leu Val Glu Ser Gly Gly Gly Leu Glu Gln Pro Gly Gly

```
1               5                   10                  15
Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
            35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
            130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430
```

-continued

Met His Glu Ala Leu His Asn His Tyr Thr Gln Lys Ser Leu Ser Leu
                435                 440                 445

Ser Leu Gly
    450

<210> SEQ ID NO 10
<211> LENGTH: 219
<212> TYPE: PRT
<213> ORGANISM: Artificial Sequence
<220> FEATURE:
<223> OTHER INFORMATION: LC

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 11
<211> LENGTH: 207
<212> TYPE: PRT
<213> ORGANISM: Artificial Sequence
<220> FEATURE:
<223> OTHER INFORMATION: hIL-4Ralpha

<400> SEQUENCE: 11

Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30

Leu Arg Leu Leu Tyr Gln Leu Val Phe Leu Leu Ser Glu Ala His Thr
        35                  40                  45

Cys Ile Pro Glu Asn Asn Gly Gly Ala Gly Cys Val Cys His Leu Leu

```
                        50                  55                  60
Met Asp Asp Val Val Ser Ala Asp Asn Tyr Thr Leu Asp Leu Trp Ala
 65                  70                  75                  80

Gly Gln Gln Leu Leu Trp Lys Gly Ser Phe Lys Pro Ser Glu His Val
                 85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
        115                 120                 125

Tyr Asn His Leu Thr Tyr Ala Val Asn Ile Trp Ser Glu Asn Asp Pro
    130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
        195                 200                 205
```